United States Patent
Paolitto et al.

(12) 
(10) Patent No.: US 6,254,532 B1
(45) Date of Patent: Jul. 3, 2001

(54) SURGICAL APPARATUS AND METHOD

(75) Inventors: Anthony Paolitto, St. Leonard; Giovanni Mannarino, Montreal; Valerio Valentini, Montreal; Bruno Zoccali, Montreal; Raymond Cartier, Town of Mount Royal, all of (CA)

(73) Assignee: Coroneo Inc., Montreal (CA)

( * ) Notice: Subject to any disclaimer, the term of this patent is extended or adjusted under 35 U.S.C. 154(b) by 0 days.

(21) Appl. No.: 09/316,133

(22) Filed: May 21, 1999

(30) Foreign Application Priority Data

May 22, 1998 (CA) .................................................. 2232795

(51) Int. Cl.⁷ ...................................................... A61B 1/32
(52) U.S. Cl. ............................ 600/201; 600/229; 600/235
(58) Field of Search .................................... 600/201, 226, 600/227, 228, 229, 235

(56) References Cited

U.S. PATENT DOCUMENTS

| | | | |
|---|---|---|---|
| 2,473,266 | * | 6/1949 | Wexler .................................. 600/215 |
| 3,221,743 | * | 12/1965 | Thompson et al. ....................... 606/1 |
| 3,278,207 | * | 10/1966 | Barish et al. ........................... 403/55 |
| 3,522,799 | * | 8/1970 | Gauthier ................................. 600/215 |
| 3,638,973 | * | 2/1972 | Poletti ..................................... 285/184 |
| 3,724,449 | | 4/1973 | Gauthier ................................. 128/20 |
| 3,749,088 | | 7/1973 | Gauthier ................................. 128/20 |
| 3,965,890 | | 6/1976 | Gauthier ................................. 128/20 |
| 4,010,741 | * | 3/1977 | Gauthier ................................. 600/234 |
| 4,813,401 | | 3/1989 | Grieshaber ............................. 128/20 |
| 5,772,583 | * | 6/1998 | Wright et al. .......................... 600/232 |
| 5,792,046 | * | 8/1998 | Dobrovolny .......................... 600/234 |
| 5,876,333 | * | 3/1999 | Bigliani et al. ....................... 600/231 |
| 5,888,197 | * | 3/1999 | Mulac et al. .......................... 600/234 |
| 5,947,896 | * | 9/1999 | Sherts et al. .......................... 600/229 |
| 5,976,080 | * | 11/1999 | Farascioni ............................. 600/213 |
| 6,042,541 | * | 3/2000 | Wexler .................................. 600/215 |
| 6,102,854 | * | 8/2000 | Cartier et al. ......................... 600/228 |
| 6,132,370 | * | 8/2000 | Furnish et al. ....................... 600/235 |

* cited by examiner

Primary Examiner—Paul J. Hirsch
Assistant Examiner—Michael B. Priddy
(74) Attorney, Agent, or Firm—Blake, Cassels & Graydon LLP

(57) ABSTRACT

A surgical apparatus is described for performing cardiac surgery on the coronary organs of a patient. It has a contacting means capable of providing a mechanical load on at least a portion of said coronary organ, a positioning means which allows the setting of either or both the contacting means and coronary organ in a large number of positions or orientations within a surgical workspace. The apparatus also has a manipulation means serving as a single point control to position and orient the contacting means onto the coronary organ tissue. An adjustment means serves to bias the range of at least one motion degree of freedom of the surgical apparatus within a the limits of a restricted range that is less than the full range of motion of that degree of freedom of motion that would be otherwise achievable when the bias is not present or overridden. This achieves the placement of the contacting means within the surgical workspace, with or without the simultaneous manipulation, retraction, or stabilization of coronary organ tissue also within the workspace. Any of the motion degrees of freedom of the surgical apparatus can be "biased". All motion degrees of freedom of the surgical apparatus are linked, whether biased or unbiased, through the manipulation means which the surgeon utilizes to set the contacting means or coronary organ tissue.

14 Claims, 30 Drawing Sheets

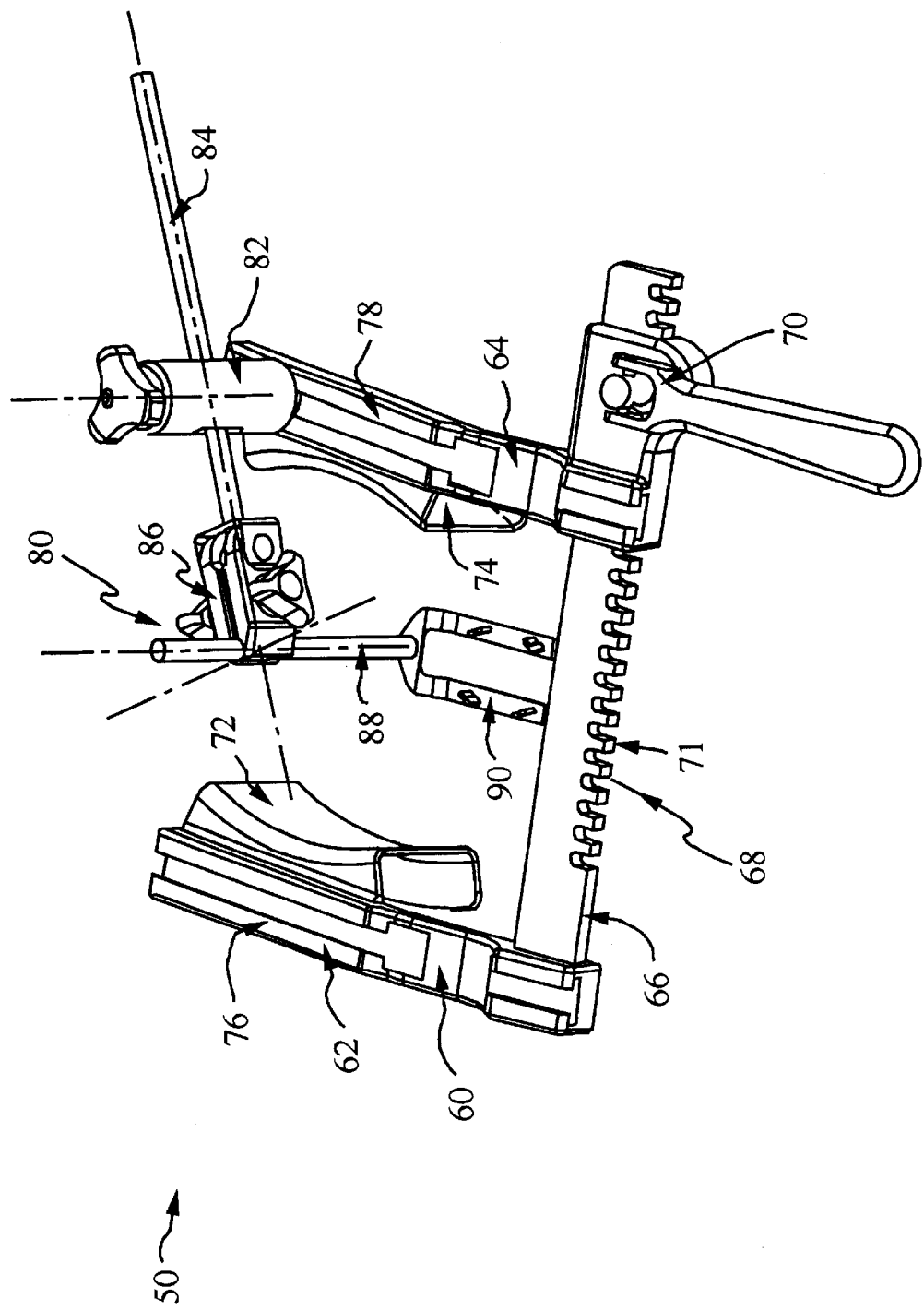

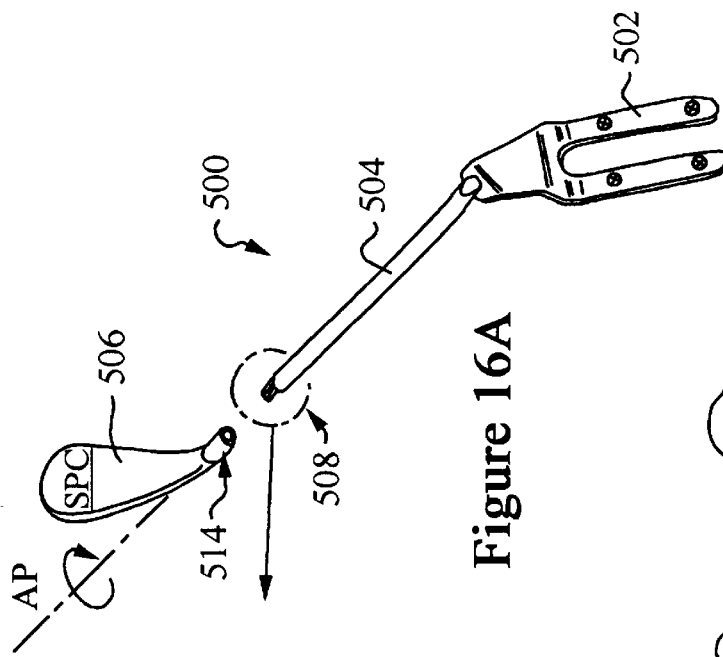
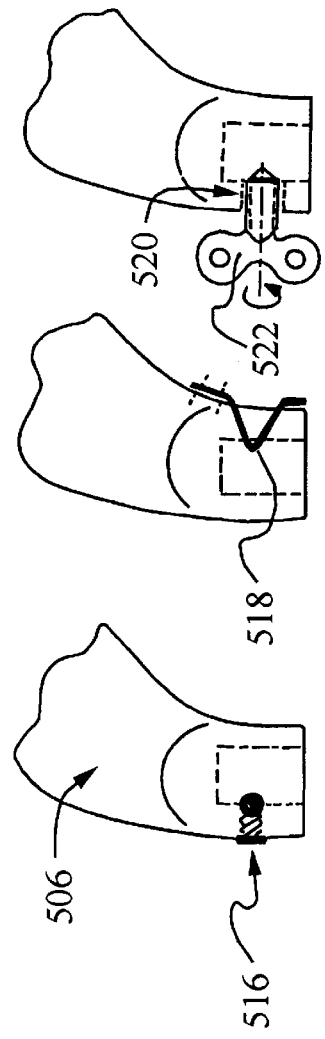
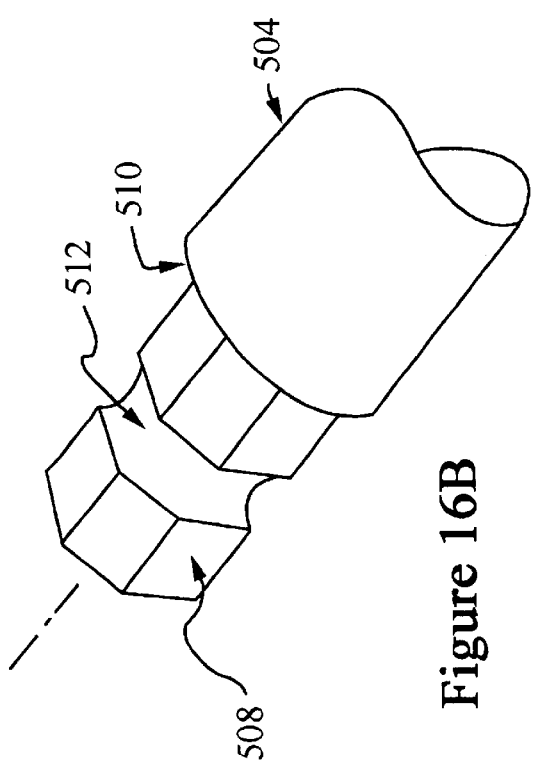
Figure 16A
Figure 16B
Figure 16C    Figure 16D    Figure 16E

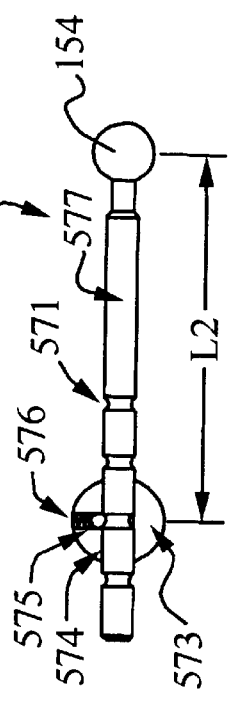
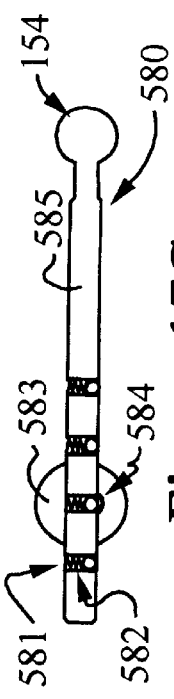
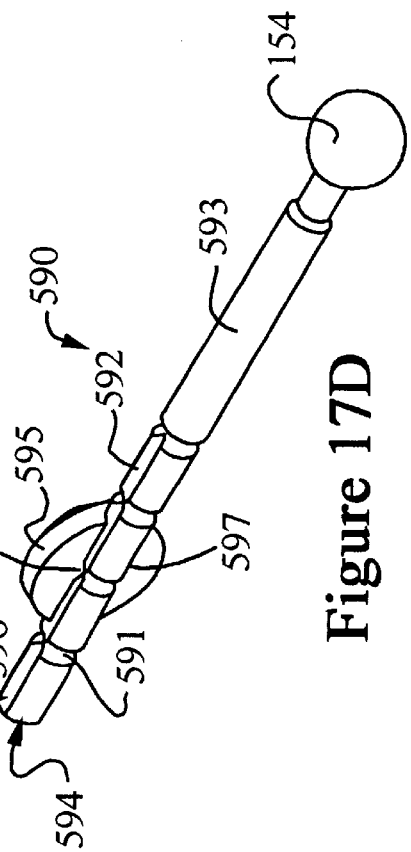
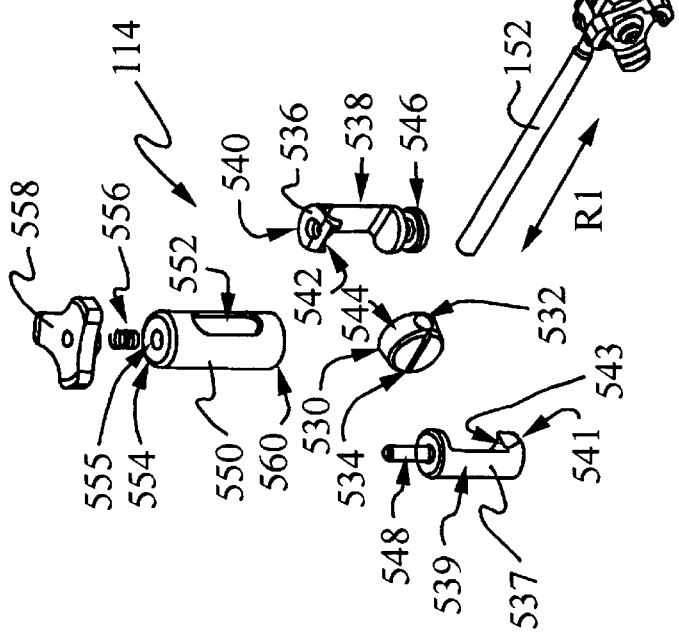
Figure 17B
Figure 17C
Figure 17D
Figure 17A

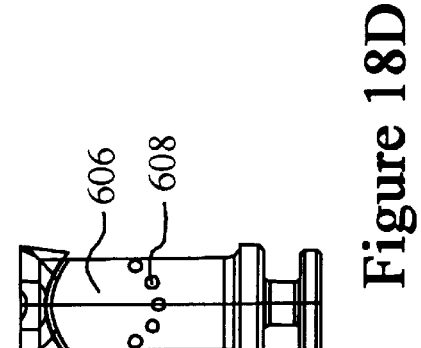
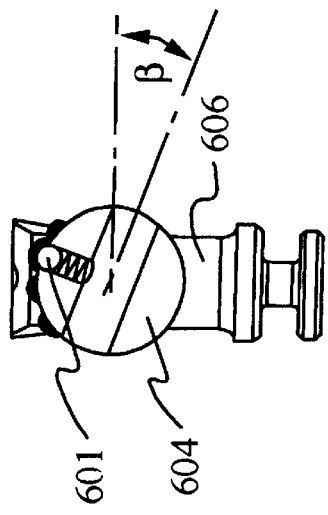
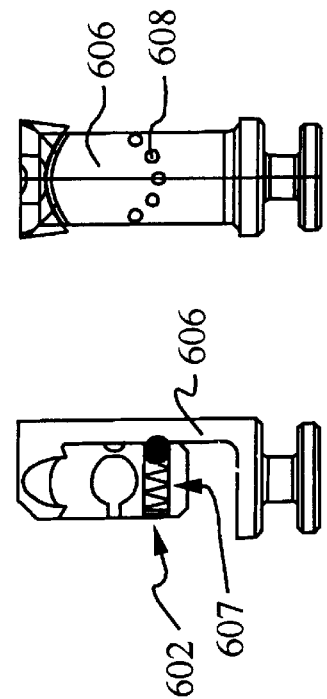
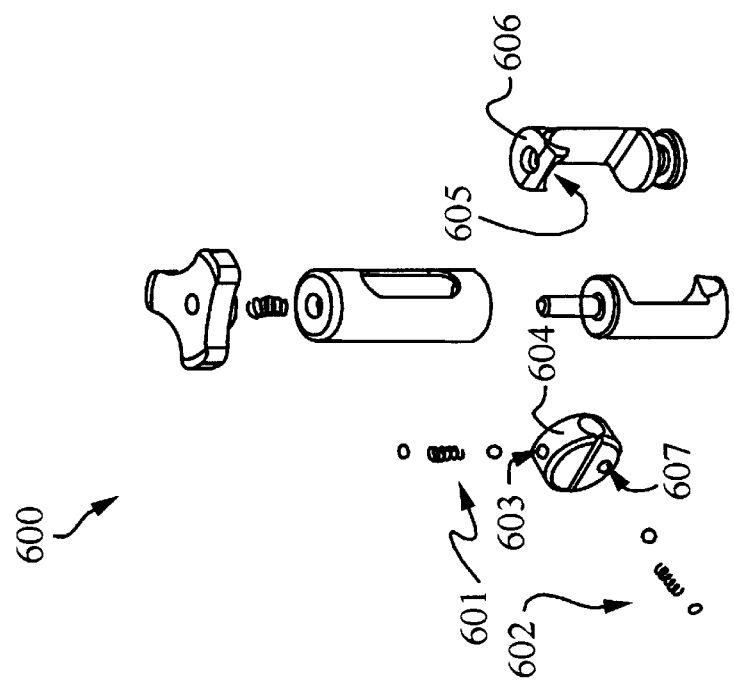
Figure 18B
Figure 18D
Figure 18C
Figure 18A

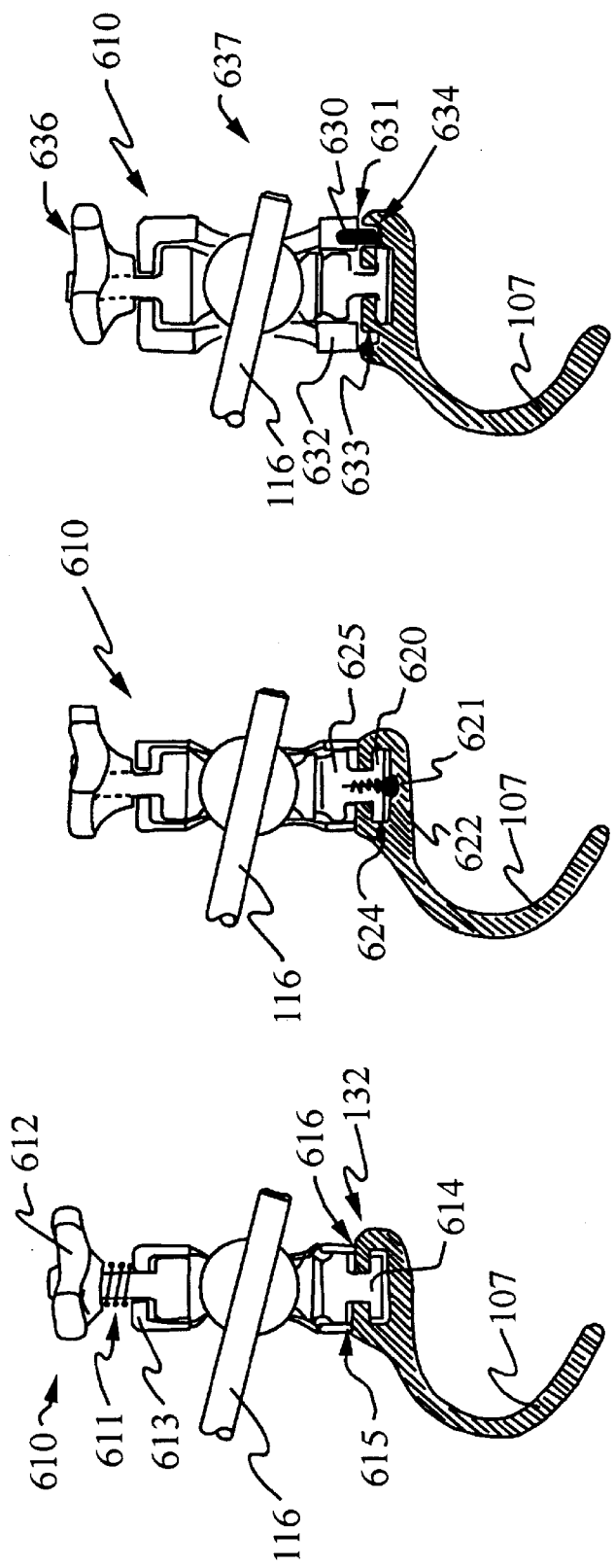

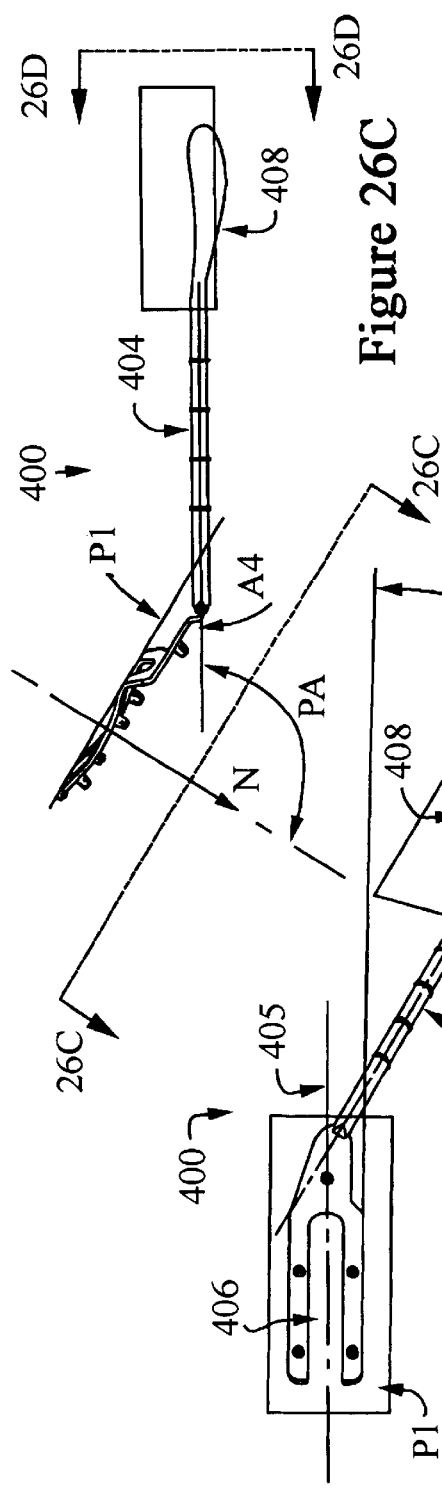
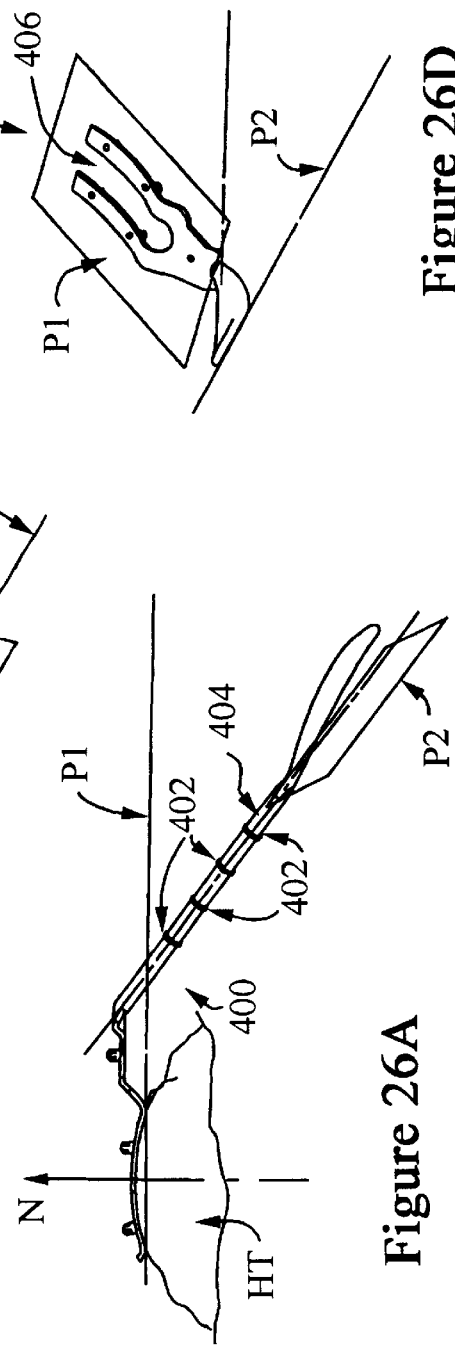
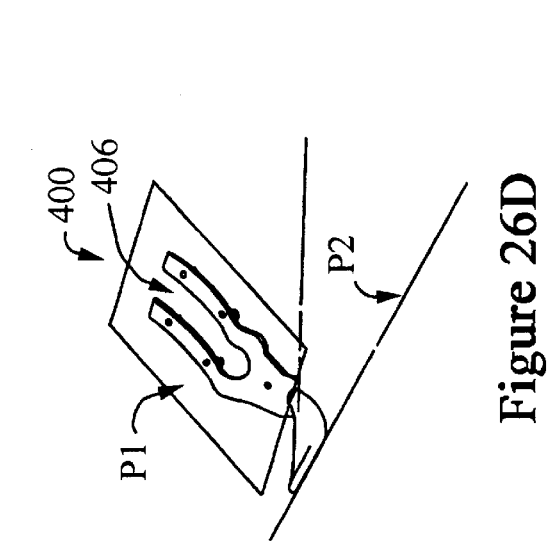
Figure 26A
Figure 26B
Figure 26C
Figure 26D

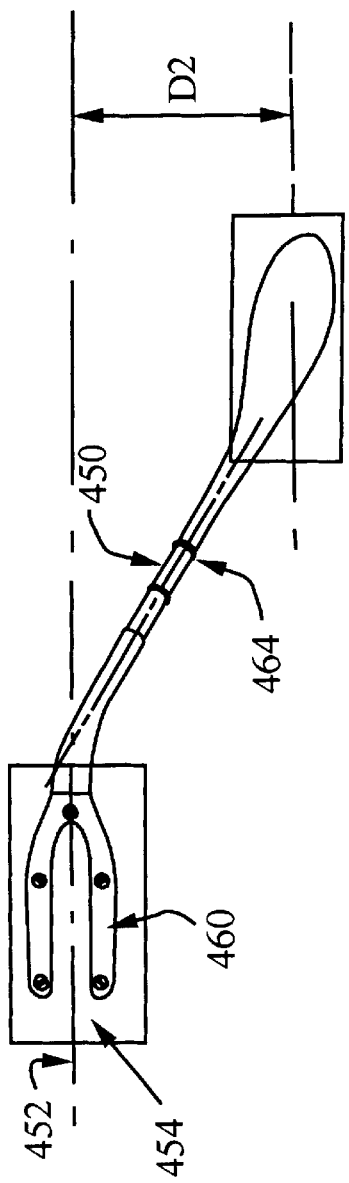
Figure 29A
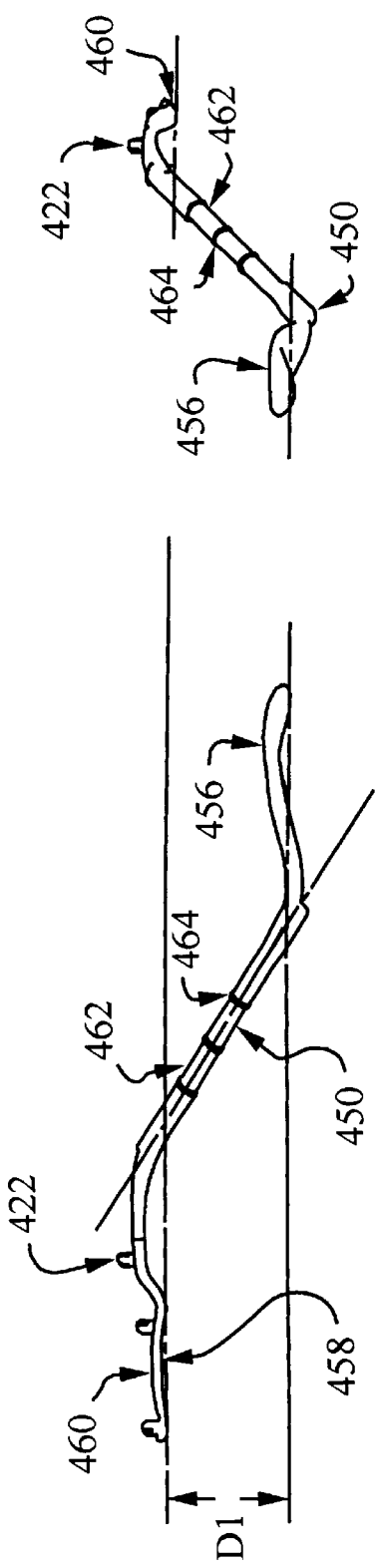
Figure 29B
Figure 29C

SURGICAL APPARATUS AND METHOD

FIELD OF THE INVENTION

The present invention relates to the field of surgical apparatus and method, such as may be used, for example, for cardiac surgery.

BACKGROUND OF THE INVENTION

Cardiac surgery includes heart surgeries that require extracorporeal circulation (ECC), that is, the assistance of the cardiopulmonary machine, and those surgeries that are performed directly on the beating heart and do not require ECC. The term "cardiac surgery" can include coronary artery bypass graft surgery (CABG) with ECC, CABG directly on a beating heart, minimally invasive direct coronary artery bypass surgery (MIDCAB), heart valve repair surgery or valve replacement surgery, and surgery to correct either an atrial septal wall or ventricular septal wall defect.

The term "cardiac devices" can include surgical apparatus and devices used during "cardiac surgery". The term "coronary organs includes the heart, the heart's arteries and veins, the surrounding tissue and vessels, in particular the mediastinum, the pericardium, the thymus, the pleura, and the space between the two lungs. In this document, unless otherwise stated, a reference to arterial surgery, or to a target artery, are intended to encompass reference to veins as well, under the general field of vascular surgery.

In recent years, the drive for cost effective surgery has intensified the need to develop surgical apparatus and medical approaches that keep healthcare costs manageable, while also allowing the treatment of older patients where economic justification may previously have been deemed marginal. Surgical apparatus that improves the efficiency of surgeons while reducing operating times, and improves the efficacy of the surgical intervention is desirable.

The recent interest in and search for less invasive surgery has placed emphasis on cardiac surgery as well. A feature of heart surgery is that the beating motion of the heart tends to complicate the delicate surgical intervention.

Heart surgeries have been performed with the support of a cardio-pulmonary machine, whereby the patient's blood was oxygenated outside the body, through extracorporeal circulation (ECC). This permits coronary operations on the arrested heart, meaning that a surgeon can manipulate and operate on a still heart. During traditional CABG surgery, this enables the surgeon to position the heart for best access to the target artery, requiring grafting.

ECC is highly invasive, particularly in coronary artery bypass graft (CABG), valvular surgery, and repair of atrial and ventricular septal wall defect. The advantages offered with ECC have been offset by the morbidity (complications) and mortality related to the ECC itself. The inflammatory response, as well as the systemic microembolisms generated by ECC, induce to some extent a dysfunctional state of the brain, lungs, and kidneys, which tends to increase with the aging of the patient. As a result, alternate CABG procedures that do not rely on the very invasive use of ECC offer distinct advantages.

Canadian patent application 2,216,893 of Cartier and Paolitto, describes apparatus for performing coronary surgery without the very invasive cardio-pulmonary machine. Canadian patent application 2,216,893 also describes surgical apparatus having "coarse" and "fine" adjustments to permit a contacting member to be placed relatively accurately in a large number of positions and orientations within a surgical working volume. The "coarse" adjustment of the heart stabilizer is achieved through linear and angular displacements, which locate a first articulation assembly in the nature of a cylindrical post on a base retractor. The "fine" adjustment of the contacting member is achieved through linear and angular displacements of a second positioning rod with respect to the first positioning rod, through a second articulation assembly.

In some cardiac interventions, it is desirable to avoid or override the coarse and fine adjustment, and to allow the simultaneous setting of all the motion degrees of freedom available in both the spherical clamp and cylindrical post, through a single point control manipulation means, thereby linking all said degrees of freedom. It is also advantageous for the contacting member, through the surgical apparatus to serve to position and orient at least a portion of the coronary organ within surgical workspace.

To achieve complete revascularization in a single surgical procedure—that is, to revascularize or treat all surgically reconstructable diseased arteries in one intervention—it may be desirable to position and orient the beating heart to obtain access to the posterior artery beds, through the same heart contacting instrument which will eventually serve to stabilize that portion of the beating heart. As a result, a surgical approach and associated apparatus which can manipulate the beating heart without inducing tissue trauma and hemodynamic instability by allowing the surgeon to exploit all motion degrees of freedom of said apparatus, through a single point control manipulation means prior to securing the entire surgical set-up, is advantageous. It is also advantageous for that apparatus to be moveable to a position in which the heart can be stabilized and in which the surgeon's field of view remains substantially unobstructed.

Prior to rigid securing of entire surgical set-up, a surgical apparatus that allows its components to remain substantially attached (while keeping their relative positions and orientations), but free to rotate, slide, and pivot when movement loads are imposed by the surgeon through the manipulation means, offers distinct advantages.

In certain surgical interventions, it may be advantageous to limit the full range of motion available in one or more of the degrees of freedom of the surgical apparatus. It would be advantageous to have an adjustment means capable of setting a "bias"—a limited range of motion within the full range of motion of that specific degree of freedom that the apparatus could otherwise achieve, were the bias not present. Furthermore, it would be advantageous to have a surgical apparatus which allows the set bias to be re-adjusted to a new setting or overridden entirely, without disengaging the constituent components used to achieve said bias, or disengage a part of the surgical set-up.

In surgical interventions, especially in a beating heart approach, where the risk of inducing heart tissue trauma is present, it is advantageous to have a surgical apparatus which enhances the sensitivity of the surgeon to the loads imposed by the contacting means on the coronary organs.

In beating heart CABG, the use of pericardial sutures are sometimes used to help "verticalize" the heart in addition to the heart stabilizer devices described in Canadian patent application 2,216,893. It would be advantageous to anchor these sutures to the base retractor or to structure outside the surgical workspace, without limiting the range of motion of the positioning means namely the articulated arm assembly, once said sutures have been set. This may tend to be beneficial in multi-vessel coronary revascularizations that require the resetting of the positioning means and at least a part of the surgical set-up, in subsequent grafting of different arteries.

In beating heart surgery, the pulsating effect of the heart on the stabilization apparatus over prolonged periods, can at times necessitate re-adjustment of the surgical set-up. In addition, the surgeon's need to vary the contact forces on the heart depending on the surgical intervention (i.e. grafting, incision, etc.), may occasionally require the re-orientation and re-positioning of the contacting means to ensure optimum stabilization during the entire surgery. Apparatus that allow easy and expedient repositioning and reorientation of the contacting means offer distinct advantages. This would be particularly so with features that facilitate use of the surgical apparatus by a person wearing surgical gloves.

It would also be advantageous to have an apparatus and method for encouraging the isolating and exposure of a target artery requiring anastomosis through the arterial window formed by the geometry of a coronary stabilizer. In beating heart surgery, the coronary stabilizer immobilizes or stabilizes a portion of the heart tissue, and consequently may tend to immobilize the target artery straddled by a coronary stabilizer. It is desirable for the target artery to be isolated and exposed in a manner that causes it to rest proudly through the arterial window of the coronary stabilizer, thereby facilitating the surgery. It would be advantageous to have a surgical apparatus of a design which may tend to reduce or minimize the amount of distortion, deflection, or restriction imposed to the underlying heart tissue, thereby tending to preserve the natural beating function of the heart under mechanical stabilization.

SUMMARY OF THE INVENTION

In an aspect of the invention there is a surgical articulation assembly. It has a first structural element having an engagement member for mating with a second structural element. The engagement member is operable in a partially engaged condition to limit a range of motion of the second structural element relative to the first structural element with respect to a first degree of freedom of motion, while permitting relative motion between the first and second elements with respect to another degree of freedom of motion. The engagement member is operable in a fully engaged condition to fix the position of the structural elements relative to each other.

In an additional feature of that aspect of the invention, the assembly includes a tightening member mounted to the engagement member. The tightening member is operable to tighten the engagement member to the partially engaged position. The tightening element is operable to lock the structural elements in a fixed position.

In another additional feature of that aspect of the invention, in the partially engaged condition the tightening member permits at least two degrees of freedom of motion between said first and second structural members. In still another feature of that aspect of the invention, in the partially engaged position the tightening member permits at least three degrees of freedom of motion between the first and second structural members. In a still further additional feature of that aspect of the invention, in the partially engaged condition the tightening member permits at least four degrees of freedom of motion between the first and second structural members. In yet another additional feature of that aspect of the innvention, in the partially engaged condition the tightening member permits at least five degrees of freedom of motion between the first and second structural members.

In another aspect of the invention, there is a surgical articulation assembly. It has a first arm, a second arm, and an articulation joint connecting said arms. The joint is engaged to said first arm. The joint has a clamp for mating engagement with said second arm. The joint and the second arm have mutually engageable indexing elements. The clamp is operable to engage the second arm in a partially tightened condition. In the partially tightened condition the indexing elements are mutually engaged to encourage the second arm to be restrained to a limited range of motion with respect to one degree of freedom of motion. In the partially tightened condition the second arm is free to move in a full range of motion with respect to at least one other degree of freedom of motion relative to the first arm. The clamp is operable to engage the second arm in a fully tightened condition to fix the second arm relative to the first arm.

In an additional feature of that aspect of the invention, the assembly is a surgical assembly. In still another additional feature of that aspect of the invention, the assembly is a surgical assembly, the second arm is a tissue stabilizing tool having a body contacting portion and a shaft portion rigidly mounted thereto and the shaft is engageable in the clamp and the clamp and shaft have features chosen from the set of (a) the indexing feature of the second arm includes at least one depression extending inwardly of the surface thereof; and the indexing feature of the clamp includes at least one protrusion for engaging the depression; and (b) the indexing feature of the second arm includes at least one protrusion extending outwardly of the surface thereof, and the indexing feature of the clamp includes at least one depression for engagement by the protrusion.

In an additional feature of that aspect of the invention, in the partially tightened condition the indexing feature of the shaft extends circumferentially thereabout to restrain longitudinal translation thereof relative to the clamp while permitting rotation about a longitudinal axis thereof relative to the clamp. In another additional feature of that aspect of the invention, one of the indexing features of the clamp or the second arm is biased to an engagement position and can deflect under an override force to permit motion outside the limited range of motion. In yet another additional feature of that aspect of the invention, one of the indexing features is a spring loaded detent.

In another aspect of the invention, there is a floating clamp assembly for governing the relationship of a first structural member to a second structural member. The clamp assembly has first and second frame members, one of the frame members being mounted in a floating relationship relative to the other. The frame members have first co-operating portions of a capture fitting for engaging a mating portion of the first structural member. The frame members have co-operating opposed jaw portions for engaging the second structural member. A retainer is mounted to limit the floating relationship between the frames and to maintain the first co-operating portions in a capture relationship with the mating portions of the first structural member. In a loosened condition of the clamp assembly, the jaw portions are biased to an engaged position relative to the second structural member by the retainer. The floating relationship permits the jaws to deflect to admit a portion of the second structural member. In a tightened condition of the clamp assembly the frame members co-operate to fix the position of the structural members relative to each other.

BRIEF DESCRIPTION OF THE DRAWINGS

For a better understanding of the present invention and to show more clearly how it may be carried into effect, reference will now be made by way of example to the accompanying drawings, which show an apparatus according to the preferred embodiment of the present invention and in which:

FIG. 2A shows a perspective view illustrating an alternative surgical apparatus for coronary revascularization on a beating heart, without ECC to that shown in FIG. 1;

FIG. 16A shows a heart stabilizer for use in the apparatus of FIG. 1 having a detachable handle;

FIG. 16B shows a detail of the stabilizer of FIG. 16A;

FIG. 16C shows an alternative securing device for the detachable handle of FIG. 16A;

FIG. 16D shows an alternative securing device for the detachable handle of FIG. 16A;

FIG. 16E shows a further alternative securing device for the detachable handle of FIG. 16A;

FIG. 17A shows an exploded view of an alternative articulated arm assembly for use in the apparatus of FIG. 1;

FIG. 17B shows a side view, in part section, of an alternative articulated arm assembly for use in the apparatus of FIG. 1;

FIG. 17C shows a side view of a further alternative articulated arm to that of FIG. 17B;

FIG. 17D shows a perspective view of part of a still further alternative articulated arm assembly to that of FIG. 17B;

FIG. 18A shows an exploded view of an alternative of a joint assembly of the articulated arm assembly of FIG. 17A;

FIG. 18B shows a side view of an element of the joint assembly of FIG. 18A;

FIG. 18C shows an end section of an alternative to the joint of FIG. 18B;

FIG. 18D shows a side view of an element of the joint of FIG. 18C;

FIG. 19A shows a section of a fitting of the apparatus of FIG. 1;

FIG. 19B shows an alternative to the fitting of FIG. 19A;

FIG. 19C shows a further alternative to the fitting of FIG. 19A;

FIG. 26A is a side view of a pull-type stabilizer for use in the apparatus of FIG. 1;

FIG. 26B is a plan view of the stabilizer of FIG. 26A;

FIG. 26C is a view of the stabilizer of FIG. 26B taken on arrows '26C';

FIG. 26D is a view of the stabilizer of FIG. 26C taken on arrows '26D';

FIG. 29A is a side view of a shallow angled pull type stabilizer for the apparatus of FIG. 1;

FIG. 29B is a plan view of the stabilizer of FIG. 29A; and

FIG. 29C is a front view of the stabilizer of FIG. 29A.

DETAILED DESCRIPTION OF THE INVENTION

Figure 1:
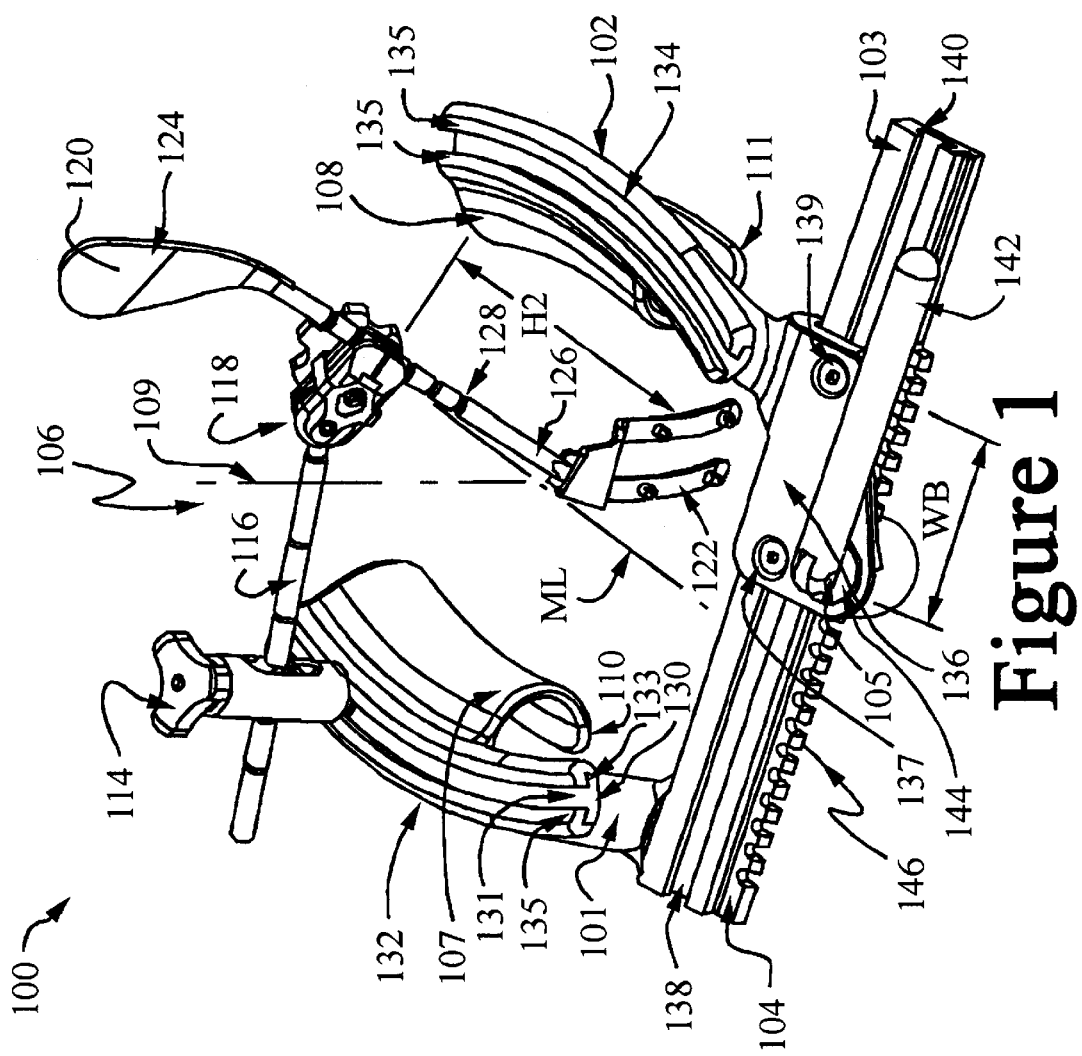
FIG. 1 shows a perspective view of a surgical apparatus according to this invention.

The description that follows, and the embodiments described therein, are provided by way of illustration of an example, or examples, of particular embodiments of the principles of the present invention. These examples are provided for the purposes of explanation, and not of limitation, of those principles and of the invention. In the description that follows, like parts are marked throughout the specification and the drawings with the same respective reference numerals. The drawings are not necessarily to scale and in some instances proportions may have been exaggerated in order to depict more clearly certain features of the invention.

Figure 2B:
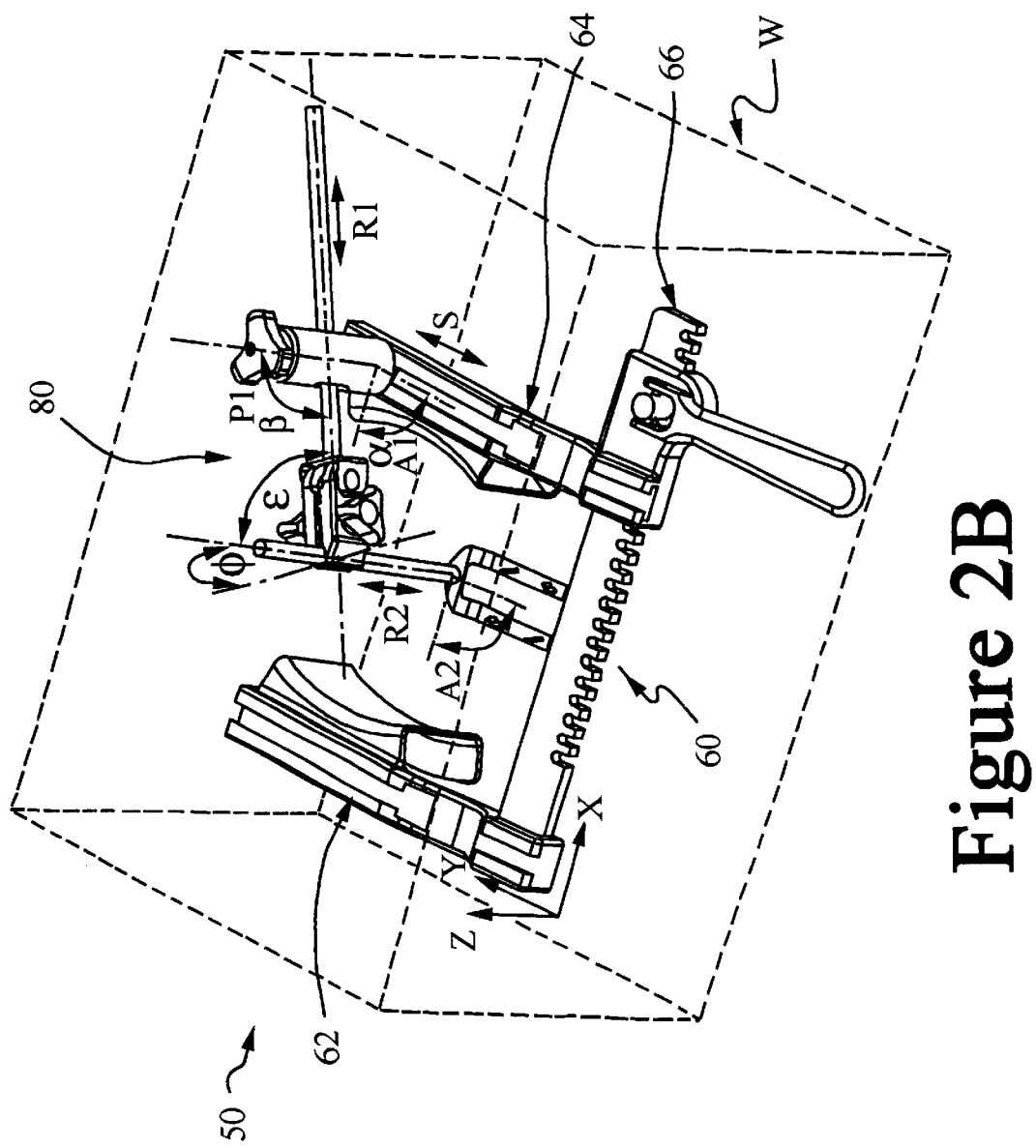
FIG. 2B shows a perspective view illustrating a working volume and degrees of freedom of motion of the surgical apparatus of FIG. 2A.

FIGS. 2A and 2B are provided for defining geometric terminology used throughout this description. A surgical apparatus is indicated generally as 50. It includes a sternum retractor 60 having a fixed, left hand structural member in the nature of a slotted channel member 62, a floating, right hand structural member 64 lying in a spaced apart, generally parallel relationship to member 62. One end of member 62 is rigidly mounted to a cross member in the nature of a yoke 66. Yoke 66 has a rack 68 along one side for engagement with a pinion 70. Pinion 70 is rotatably mounted to one end of right hand structural member 64 such that operation of the handle of pinion 70 engaging the teeth 71 of rack 68 will cause translation of member 64 relative to rack 68 in a direction indicated as the 'x' direction, thereby adjusting the spacing between members 62 and 64. Left and right hand arcuate sternum retractor blades or clamps 72 and 74 depend from members 62 and 64 respectively, and, when members 62 and 64 are driven apart clamps 72 and 74 are operable to engage and separate left and right sides of a patient's rib cage. Each of members 62 and 64 has a rail, or trackway 76, 78 in the nature of a slot defined in the upper surface thereof.

A multiple degree of freedom articulated arm assembly is indicated generally as 80. It has a first, main, or shoulder joint indicated generally as 82 having a footing engaged in trackway 78. Shoulder joint 82 is also referred to as a cylindrical post, and is described in greater detail below. A first, or upper arm 84 extends from joint 82 to a second, intermediate, or elbow joint, indicated generally as 86, and a second, lower, or forearm 88. Elbow joint 86 is also referred to as the second articulation member, or as the spherical clamp. Several embodiments of spherical clamp elbow joints are described in greater detail below. A body engaging, tissue stabilizing member, or hand, indicated generally as 90 is rigidly mounted to the distal end of forearm 88.

Referring now to FIG. 2B, the flexibility and versatility of surgical apparatus 50 is described with reference to the following degrees of freedom:

S.: displacement of first articulation member along rails of retractor

R1: axial displacement along centerline of first positioning rod through first articulation member R2: displacement along centerline of second positioning rod through second articulation member α: rotation about centerline of first articulation member assembly A1: angular displacement through rotation α

β: angle between centerline of first positioning rod and centerline of articulation member assembly P1: displacement along z axis achieved through rotation β

ε: angle of tilt between (a) a plane containing the longitudinal axis of the second positioning rod and a horizontal axis perpendicular to the centerline of the first positioning rod, and (b) the centerline of the first positioning rod φ: slew angle between the longitudinal axis of the second positioning rod and the horizontal axis perpendicular to the centerline of the first positioning rod, the slew angle lying in the plane containing both the longitudinal axis of the second positioning rod and the horizontal axis perpendicular to the centerline of the first positioning rod A2: angular displacement of contacting means about the centerline of second positioning rod Referring more specifically to FIG. 1, a surgical apparatus is indicated generally as 100. It has a fixed left-hand main structural member 101, a floating right-hand main structural member 102. A yoke 103 is rigidly connected to member 101. Yoke 103 has a rack 104 that interacts with pinion 105 of member 102. An articulated arm assembly is indicated generally as 106. It has a main, or shoulder joint 114 mounted to left hand member 101. A first or upper arm 116, is mounted in, and extends from, shoulder joint 114 to a second, intermediate, or elbow joint 118. A heart stabilizer tool is indicated generally as 120. It has a body contacting member, in the nature of a bi-furcated hand 122 for engaging a body part of a surgical patient, such as the heart; a manipulation member, in the nature of a broadened and flattened handle, 124; and a rod, or shaft 126, intermediate and rigidly connected to hand 122 and handle 124. Shaft 126 has an array of circumferential reliefs, or grooves 128 spaced along its length. Shaft 126 is engageable in elbow joint 118 to perform the function of a second, lower, or forearm element of assembly 106. Each of these major elements will now be described in greater detail.

Structural members 101 and 102, and yoke 103 combine to form the major elements of a strenum retractor for maintaining the chest cavity of a patient in an open position. Yoke 103 extends in a direction defined as the 'x' direction, and members 101 and 102 extend away from it, the bisector 'ML' lying between members 101 and 102 extending away from yoke 103 in the perpendicular, 'y' direction. Each of members 101 and 102 has a depending grip 107 or 108 for engaging one side or other of a patient's rib cage. As shown, each grip 107 or 108 has a compound curvature, having the form of an outwardly facing portion of a curved roll. The main axis 109 of the roll lies in the 'z' direction, while the radius of curvature of any section of the roll lies on an arc lying in an x-y plane. Each of the depending corners 110, 111, or the rolled skirt is smoothly and generously radiused to reduce the tendency of the grip to tear at the patient's tissue.

Each of members 101, 102 terminates in a rail, or trackway in the form of an integral, arcuate channel 132, 134 having a widened, substantially rectangular inner portion 130, and a narrower throat 131, such that the shoulders 133 of the overhanging flanges of the wider portion are capable of capturing a mating engagement fitting in the nature of a foot of shoulder joint 114, as described below. The arc of channel 132, 134 has a common center of curvature with its respective depending grip 107, 108.

The base of floating right hand main structural member 102 is rigidly mounted to a carriage member 136 for engagement with yoke 103. In the preferred embodiment carriage member 136 and structural member 102 are formed integrally as a unitary, titanium cast part. Similarly, in the preferred embodiment structural member 101 and yoke 103 are formed as a unitary titanium casting. Yoke 103 has a rail, or guide in the nature of trackway 138 formed therein. Trackway 138 has substantially the same cross section as channels 132 and 134 such that objects, such as joint or tool fittings that can engage one of them can also engage any of the others. Carriage member 136 has a pair of guide wheels 137, 139, in the nature of bearings of a size for running in close engagement in trackway 138, the shoulders of the bearings being captured by overhanging flange shoulders 140 of trackway 138. Pinion handle 142, is pivotally mounted to the head of a cogged pinion shaft 144, that interacts with the teeth 146 of rack 104, thereby permitting carriage member 136 to be driven away from or toward member 101. The longitudinal spread, or wheel base, of wheels 137, 139, indicated as 'WB' provides a relatively lengthy moment arm for reacting moments due to force couples exerted by the rib cage on members 101 and 102. The use of close fitting bearings tends to enhance the smoothness of operation of the mechanism, and may reduce the tendency of the pinion hand to bear a portion of the moment from members 101 and 102. That is, the wheels may tend to react to the moment, and may tend to reduce the burden on the ratchet as it drives carriage member 136 along rack 104.

Figure 3:
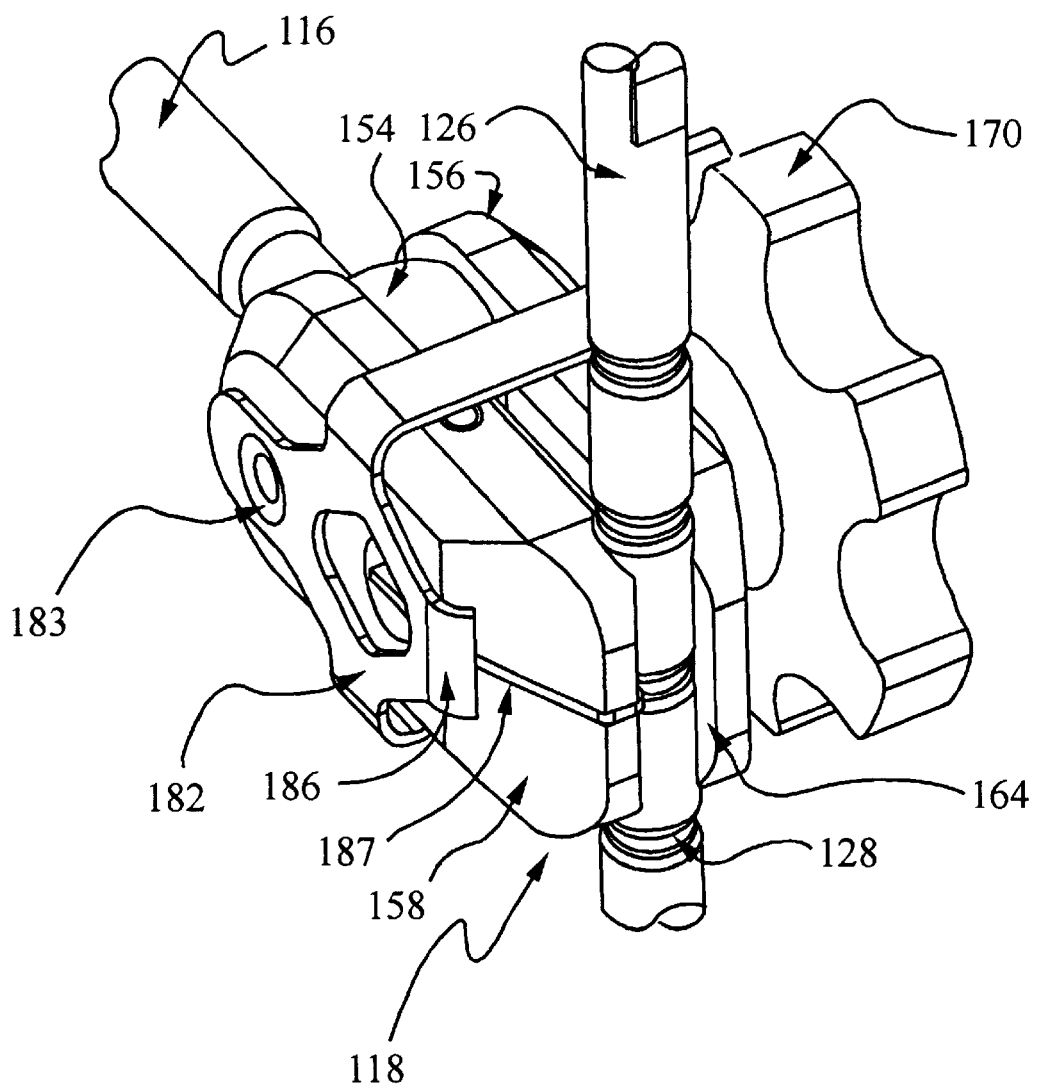
FIG. 3 is a perspective view of a detail of an articulation member and adjustment member of the surgical apparatus of FIG. 1.
Figure 4:
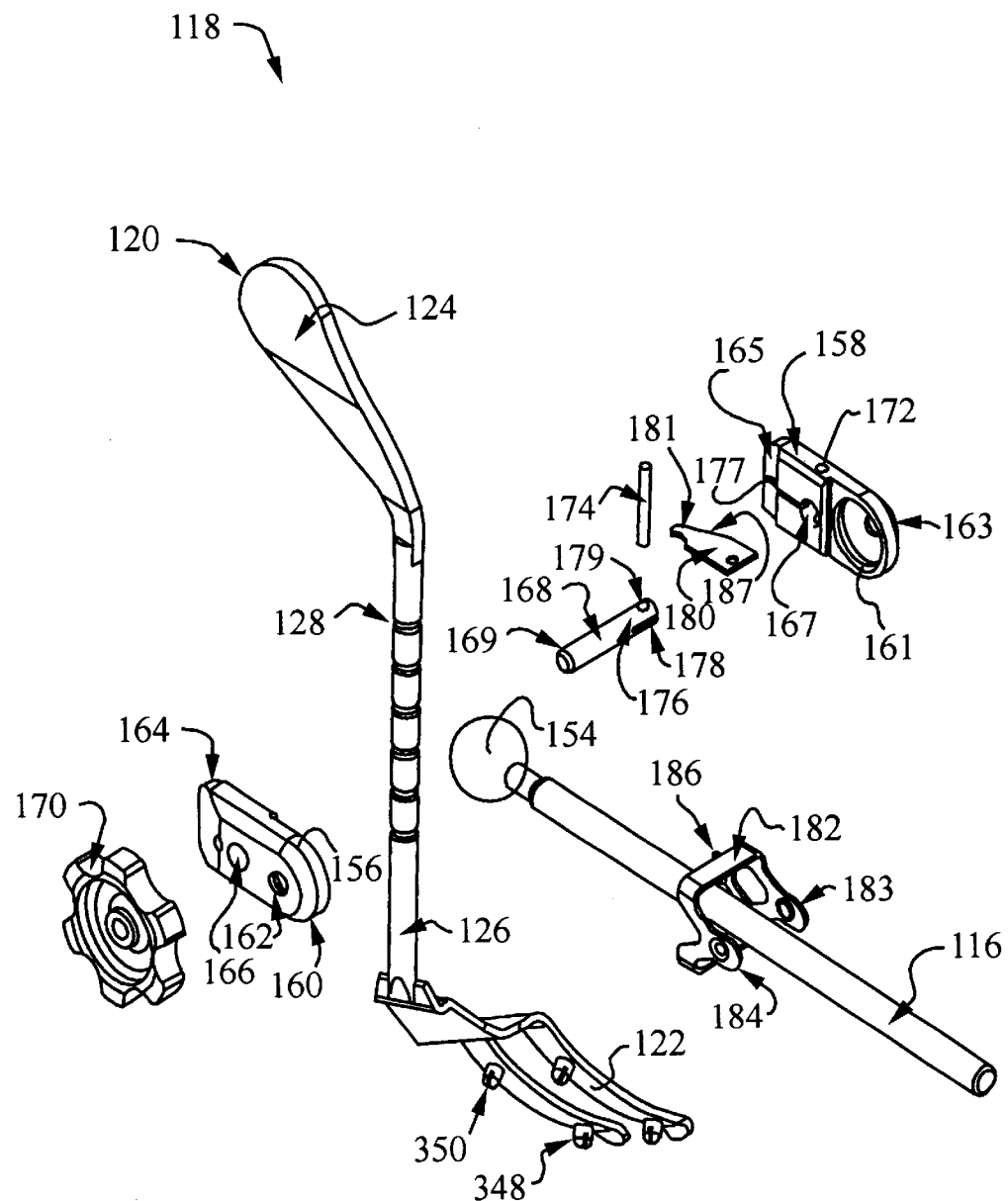
FIG. 4 is an exploded view of the members of the surgical apparatus of FIG. 3.

Referring now to the articulated arm assembly indicated generally as 106, elbow joint 118 is shown in greater detail in FIGS. 3 and 4. Elbow joint 118 is a clamping assembly that interacts with a spheroidal distal end termination 154 of upper arm 116. Elbow joint 118 has a pair of left and right hand clamp side-frames 156 and 158, each having a spherical arc socket 160, 161 for engaging termination 154. Each socket 160, 161 has, at the polar extremity thereof, an inwardly extending feature, in the nature of an aperture, or hole, 162, 163. At their respective distal ends, each of side-frames 156 and 158 have a jaw 164, 165 for tightening against shaft 126 of handle 124. The bodies of each of side-frames 156 and 158 have a main bore 166, 167 formed therethrough to admit a common central shaft 168 that is threaded at one end 169, to mate with a threaded tightening member, or knob, in the nature of an internally threaded, castellated thumb wheel 170. Right hand side-frame 158 also has a perpendicular bore 172 bored therethrough to intersect bore 167, bore 172 being of a lesser size than bore 166 such that a cotter pin, or roll pin or a dowel pin 174 can be introduced therethrough, in alignment with a co-operating bore 179 in end 176 of shaft 168, thereby connecting these members.

Jaw 165 is bifurcated by a slot 177 that extends inwardly from jaw 165 to bore 167. Shaft 168 has a co-operating slot 178 that is, in use with pin 174 in place, extending through bore 179 aligned with slot 177 to admit a detent engagement member, in the nature of a toothed dog, 180. Dog 180 has a bore formed therein to admit pin 174, such that dog 180 can pivot about pin 174, in a manner that permits its tooth, 181, intermittently to engage such of grooves 128 as it may encounter. A retainer, or resilient biasing member, or spider, in the nature of a pre-loaded, formed steel spring 182 has a pair of ears 183, 184 having inwardly formed dimples for location in holes 162, 163 respectively. When so located, spring 182 encourages sockets 160, 161 to remain engaged with termination 154, whether thumb wheel 170 is tightened or not. An inwardly curved spring tang 186 is located at the jaw-ward extremity of the right hand side of spring 182, and is positioned to bear inwardly on the outward spine 187 of dog 180 to urge tooth 181 toward a position to ride against shaft 126, and to engage one or another of grooves 128 as the opportunity arises.

In the preferred embodiment (FIGS. 3 and 4), as described, dog 180 acts as an adjustment means, or adjustment lever which engages an adjustment feature, in shaft 126, namely one of grooves 128. As noted, dog 180 partially rests in planar slit, or slot, 177 in clamping side-frame 158, and the axial slit, that is, slot 178, in the clamp tensioning stud, that is, common central shaft 168. The faces of slot 177 serve as a channel to guide the lever, dog 180, through a substantially planar rotation about the centerline of retention pin 174, once the clamp assembly, that is, elbow joint 118, is completed by inserting retention pin 174 through bore 172, through retention stud bore 179, of shaft 168, and through the lever, dog 180.

Subsequently, the two clamping member side frames 156 and 158 are assembled with the interfaces of sockets 160, 161 in contact with the spherical end 154 of the first articulation rod, shaft 116. Preloaded spring 182 secures the spherical clamp in a state of "light-tightness" through the dimples of ears 183, 184. The tensioning knob, wheel 170, is screwed onto the portion of shaft 168 extending through clamp member side frame bores 164 and 166, but not tightened, in order not to override the "light-tightness" effect of spring 182 due to its pre-load. Light-tightness, or pre-loading in this way, permits the components of the surgical apparatus to stay substantially attached, and loosely in place relative to each other (while keeping their relative positions and orientations), but free to rotate, slide, and pivot when movement loads are imposed by the surgeon through a manipulation means, such as exemplified by handle 124. That is, under the spring pre-load, the assembly has a first, or partially tightened, level of tightness, a "light-tightness", in which the static forces in the objects are sufficient to maintain the various elements of the upper arm, elbow joint, and hand in position relative to each other under their own weight, while still permitting manipulation. Then, using the tightening knob, wheel 170, the elbow joint assembly can be tightened to a second, of fully tightened condition for transmitting operational loads between shaft 126 and upper arm 116 during surgery.

Once the spherical clamp, that is, elbow joint 118, is fully assembled, the extending feature, tang 186 of spring 182 rests flush against the outside face of clamping member side-frame 158, and does not impose a spring load on the lever, dog 180 when either (a) there is no stabilizing tool shaft between jaws 164 and 165 or (b) when there is a stabilizing tool shaft between jaws 164 and 165 and tooth 181 is engaged in one of grooves 128. In this position, spine 187 of the lever, dog 180, is also flush with outside face of clamp side-frame 158, but tooth 181 extends proudly from the inside surface of jaw 165, ready to engage any of grooves 128 on the incoming rod, shaft 126, either as it is introduced into jaws 164 and 165 radially relative to spherical end termination 154, or when sliding longitudinally along the longitudinal axis of shaft 126.

Spring 182 also keeps the two clamping members spread apart ready to receive shaft 126, and maintains them in set position with respect to articulation rod, that is, upper shaft 116 without "droop" by virtue of the imposed spring pre-load. As shaft 126 snaps into the substantially cylindrical volume created by the two surfaces of jaws 164 and 165, the two clamping members first spread apart further, while rotating about spherical end termination 154, and then resume their original position. The surfaces of sockets 160, 161 remain in contact with spherical end termination 154 throughout.

The adjustment lever, dog 180, behaves independently of the loading function of spring 182 which keeps clamping member side-frames 156 and 158 in "light-tightness" against spherical end termination 154, through its extending feature, tang 186. When the dog 180 is engaged in one of grooves 128, the adjustment means thereby achieves a bias. That is, the joint is urged to one position, or a limited range of positions, in respect of one of its degrees of freedom, within the overall range of motion that is could otherwise achieve were that range limiting means, typically a detent, or series of detents, such as provided by the interaction of dog 180 with grooves 128, not present. For example, the linear motion degree of freedom R2 of shaft 126 relative to jaws 164,165 can be limited to a setting of H2, corresponding to the second groove 128, while elbow joint 118 can tend to be manipulated with respect to the full range of all of its other degrees of freedom, such as rotation A2 about the axis of shaft 126, rotations $\phi$ and $\epsilon$ relative to end termination 154.

The profile of the annular groove adjustment feature, that is, the profile of each of grooves 128, allows repositioning of the heart contacting means, namely hand 122 along R2 to a different H2 bias, without disengaging shaft 126 from the spherical clamp of elbow joint 118. To modify the bias H2, the surgeon needs to push or pull shaft 126 through the elbow joint 118, preferably by grasping, and pulling or pushing the manipulation means, namely handle 124, thereby overcoming the resistance of the detent of the adjustment means, namely the engagement of tooth 181 and groove 128 under the urging of tang 186. Groove 128 has a sloped shoulder profile, to act as a wedge or cam surface in such a manner that the translation of shaft 126 along it longitudinal axis, between jaws 164 and 165 eases tooth 181 of the adjustment lever, dog 180, radially outward from its centerline as dog 180 pivots about pin 174, forcing spine 187 progressively against the resisting spring load imposed by tang 186 of the spring 182. Once the next adjustment feature, namely the next groove 128 on shaft 126 reaches the spring feature, tang 186, again urges tooth 181 into groove 128. The contacting means, hand 122, can still rotate through angle A2, the entire spherical clamp and shaft 126 can pivot through angle $\epsilon$, and can rotate $\phi$ with respect to upper arm 116, but the linear motion along R2 is biased to H2 by the detent type adjustment means of dog 180, tang 186 and grooves 128.

Tightening the tensioning knob, wheel 170, on the threaded retention stud, shaft 168, to a second, operational tightness level, serves rigidly to fix, in a given orientation and position, all degrees of freedom of motion of the spherical clamp of elbow joint 118, by imposing clamping loads on the shaft 126 and spherical end termination 154, thereby overriding the "light-tightness" load of spring 182.

Although only one detent device is shown in the preferred embodiment of FIGS. 3 and 4, a second dog-and-spring mechanism could be mounted to the left hand clamp side frame, without its pivot pin intersecting central shaft 168.

Figure 5:
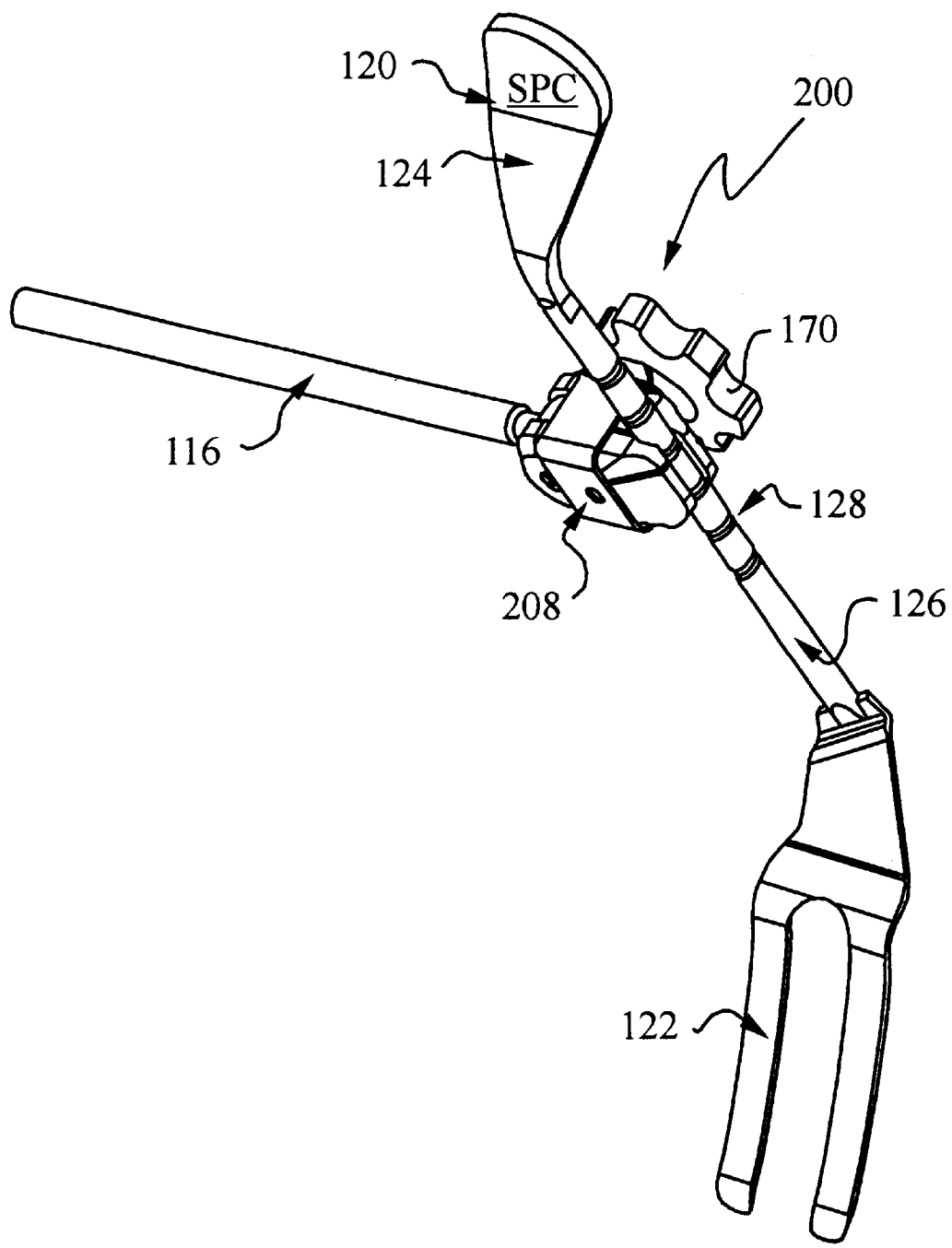
FIG. 5 is a perspective view illustrating an alternative apparatus to the apparatus of FIG. 1.
Figure 6:
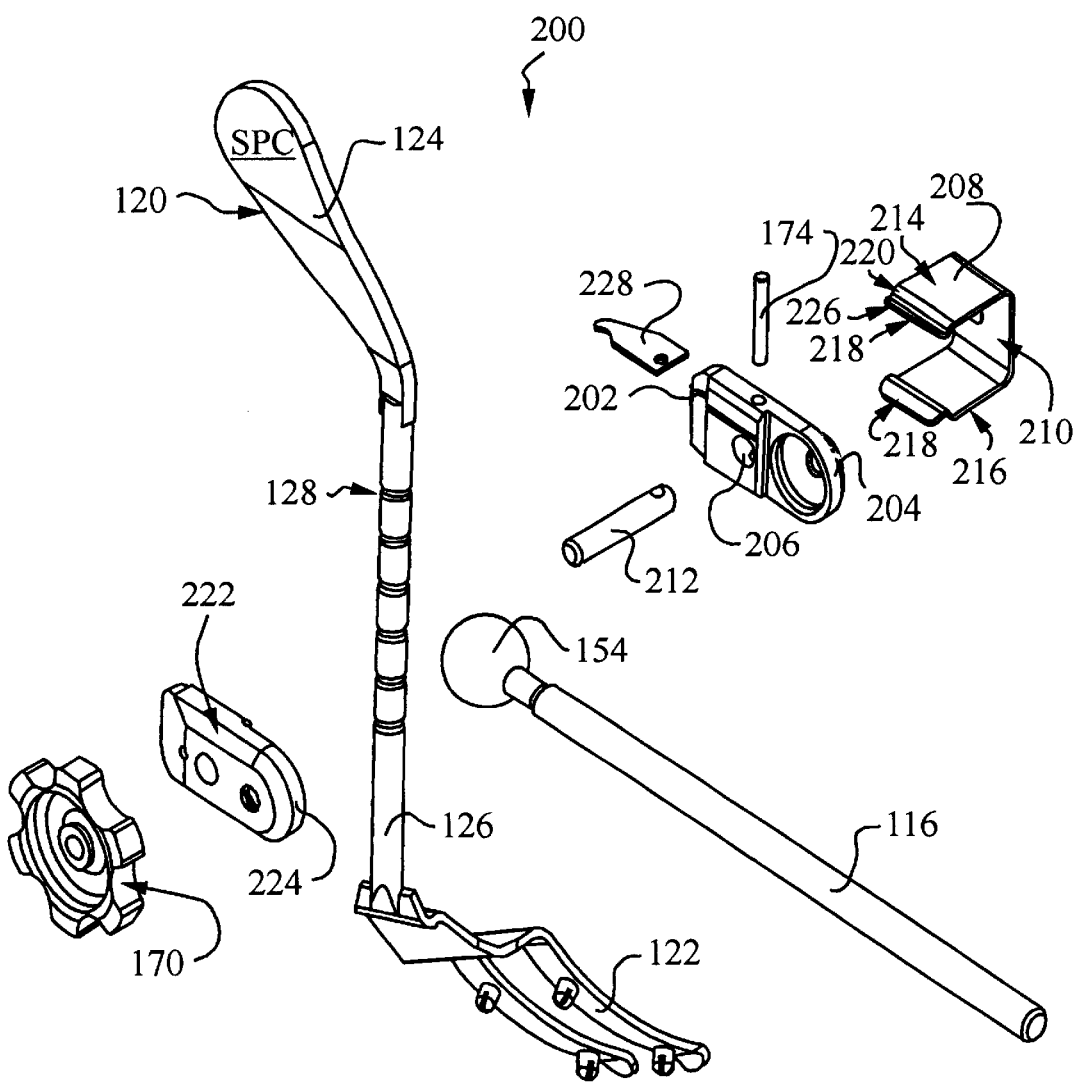
FIG. 6 is an exploded view of the alternative apparatus of FIG. 5.

FIGS. 5 and 6 illustrate an alternative to elbow joint 118. Spherical clamp elbow joint 200 differs from elbow joint 118 inasmuch as a dog accommodating slot 202 formed in right-hand side-frame 204 lies at a level to clear main shaft bore 206. Spring 182 is replaced by a generally U-shaped channel-like spring 208. Spring 208 is a resilient clip, having a back 210 with an aperture for alignment with main central threaded stud shaft 212, and a pair of toes 214 and 216 extending substantially perpendicularly therefrom. Toes 214 and 216 each terminate at a distal catch 218, having a steep inward shoulder 220 for engaging chamfered shoulder 222 of the opposite, left hand side-frame 224, and a ramp 226 extending from shoulder 220 that acts as a cam or wedge to facilitate the flexing of spring 208 to open, permit entry, then close inwardly about the other elements of elbow joint 200.

The adjustment lever, dog 228, rests entirely in slot 202 of clamping member side-frame 204, and is energized by a different type of spring 208. Spring 208 also has the function of maintaining the two clamping members, side-frames 204 and 224 at a first level of tightness, light tightness as described above, against spherical end termination 154 of upper arm 116. Catches 218 of spring 208 are intended to facilitate assembly of two clamping members onto spherical end termination 154. The threaded clamping stud, main central shaft 212, unlike shaft 168, does not have a slot such as slot 178.

Figure 7:
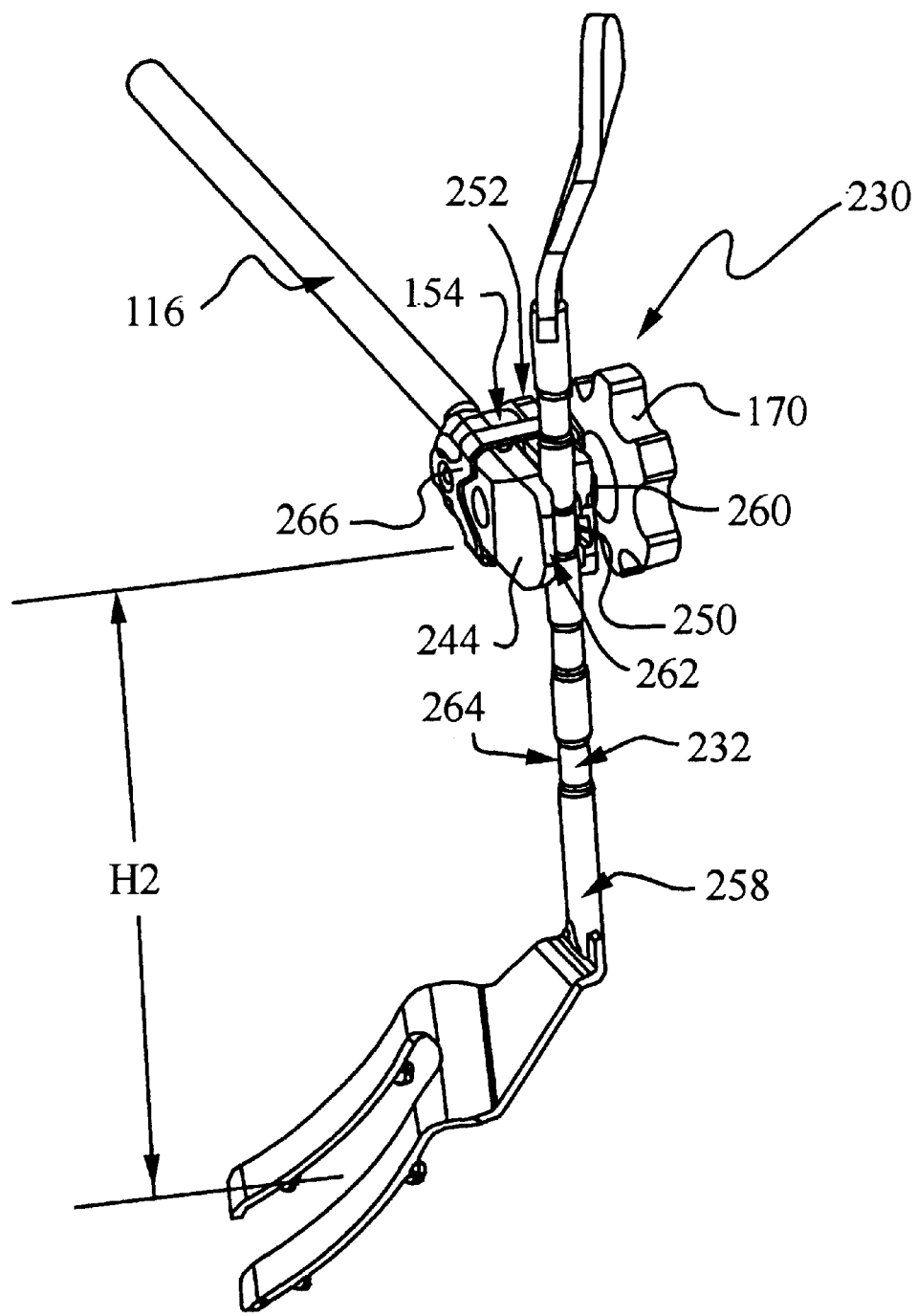
FIG. 7 is a perspective view of another alternative to the members of FIG. 3.
Figure 8:
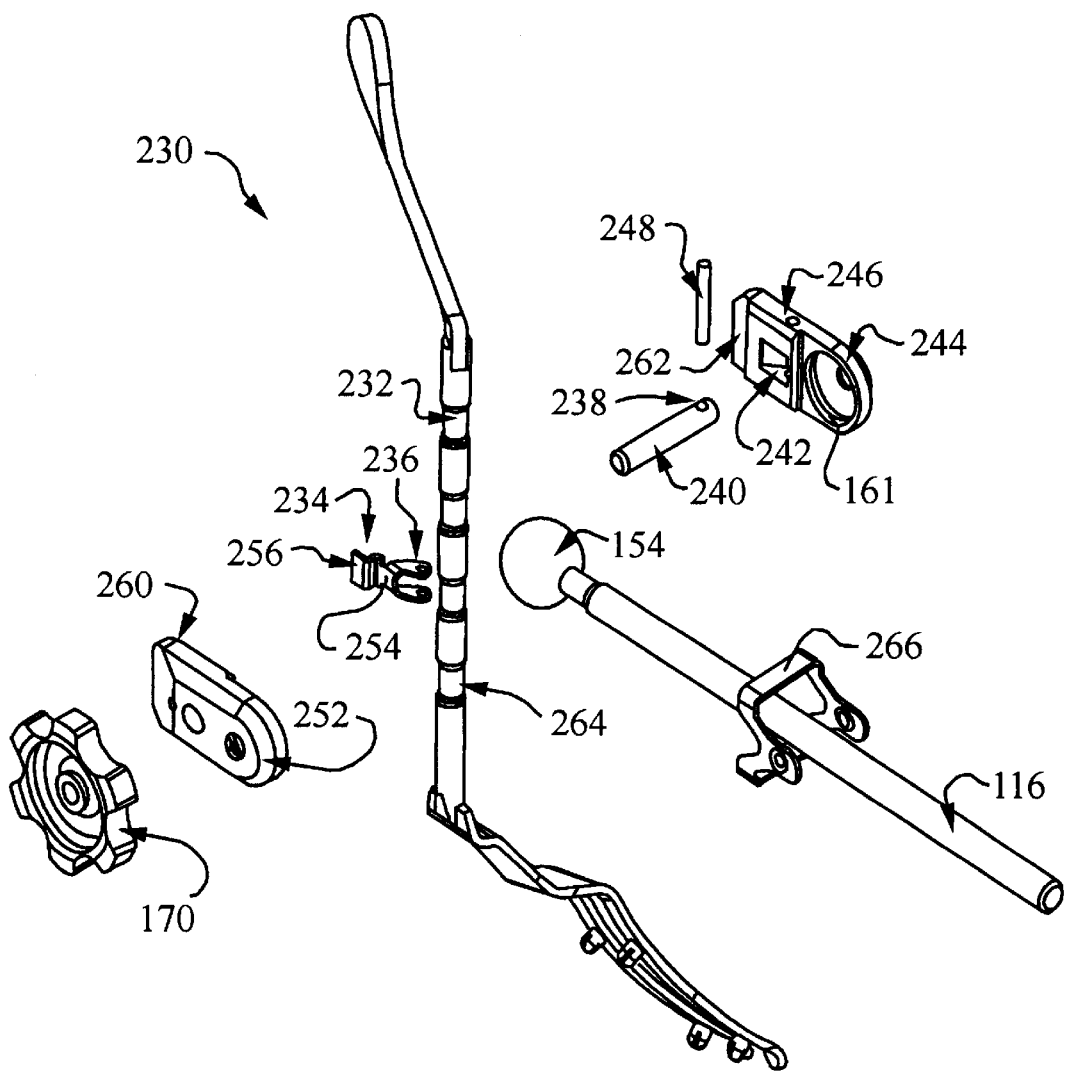
FIG. 8 is an exploded view of the alternative members of FIG. 7.

FIGS. 7 and 8 illustrate another alternative embodiment elbow joint for use in an apparatus such as the apparatus of FIG. 1. In this example, heart stabilizer tool 120 is replaced by a generally similar heart stabilizer tool 230, in which circumferential grooves 128 are replaced by circumferential waists, in the form of substantially square shouldered rebates 232, the width of each rebate being greater than its depth. The adjustment means in the embodiment of FIGS. 7 and 8 includes a formed spring 234 having a pair of protrusions in the form of a clevis 236 for seating in alignment with a bore 238 in main central threaded stud shaft 240. A chamber 242 for accommodating clevis 236 is defined inwardly of the inner wall of right hand clamp side-frame 244. A cross bore 246 is formed in side-frame 244 to permit the introduction of a hinge in the nature of a cotter or roll pin 248, analogous to pin 174. Another chamber, in the nature of an inwardly extending slot 250 is defined in the inner wall of left-hand side frame member 252. An intermediate surface 254 of spring 234 backs, or rests against the inside face of clamping member side-frame 252. A cantilevered deflection member, in the nature of a bent tongue 256, extends from surface 254 generally away from clevis 236 to seat in slot 250. When tongue 256 engages slot 250, jaws 260 and 262 engage the larger diameter portions of shaft 258 lying to either side of rebate 232. When shaft 258 is engaged by jaws 260 and 262 of clamping member side-frames 244 and 252, the cantilevered portion, that is tongue 256, of spring 234 is deflected and thereby applies a load against the waist surface 264 of rebate 232, thereby achieving the desired H2 bias. The profile of the spring element spring 234, and the surface 264, allow the translation of shaft 258 through the spherical clamp elbow joint, thereby re-adjusting the bias without having to disengage components. Main retainer spring 266 is generally similar to spring 182, but lacks tang 186.

Figure 9:
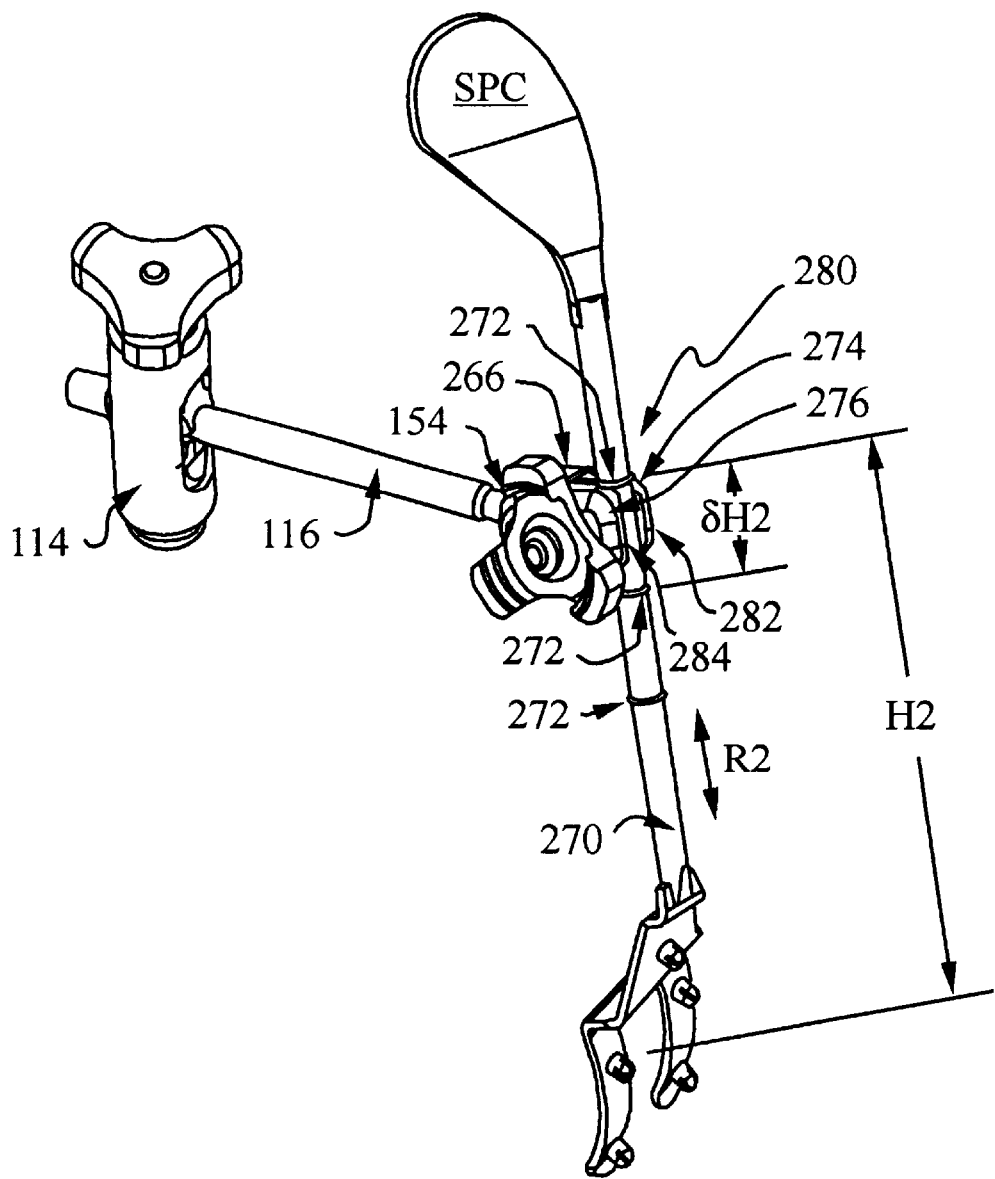
FIG. 9 is a perspective view of an alternative embodiment to the apparatus of FIG. 1.

FIG. 9 illustrates another alternative embodiment of elbow joint. Shaft 270 is provided with an array of spaced, outwardly extending cirumferential ridges 272. The spacing $\delta H2$ of these ridges is greater than the height dimension of side frames 274 and 276 of elbow joint 280. The elements of elbow joint 280 are generally similar to the elements of elbow joint 200, with the exception that elbow joint 280 does not have an internal spring-and-detent type mechanism. Rather, spring 182 is replaced by a spring such as spring 266. The shoulders of ridges 272 have a profile, that is, they are tapered, to cause jaws 282 and 284 to yield, moving outwardly against the resistance of spring 266 when shaft 270 is pushed sufficiently hard in the R2 direction, or is introduced or removed from jaws 282 and 284 by translation perpendicular to R2 with sufficient force to overcome the resistance of spring 266. In an alternative embodiment, the inner upper and lower edges of jaws 282 and 284 could be tapered to yield a wedge, or cam-and-cam follower relationship with ridges 272.

In this example, the bias H2 is variable within the limited range set by two adjacent discrete ridges 272, as a subset of the overall range of motion in the R2 direction along shaft 270. The further apart the ridges, the wider the limit in bias $\delta H2$ within entire range of motion R2. The bias H2 can be re-adjusted beyond the range $\delta H2$ by translating shaft 270 through the spherical clamp of elbow joint 280, thereby situating the clamp between the next two adjacent ridges 272. As noted, the profile of ridges 272 is such that it eases apart the two clamping members, as they rotate over spherical end termination 154 while maintaining contact therewith under the urging of spring 266. As before, this allows shaft 270 to translate through elbow joint 280. Unlike previous embodiments, this third embodiment allows shaft 270 to slide freely within range $\delta H2$, in addition to rotating in the A2 direction and pivoting in the $\epsilon$ and $\phi$ directions freely while in the first level of tightness, or "light-tightness" state.

Figure 10:
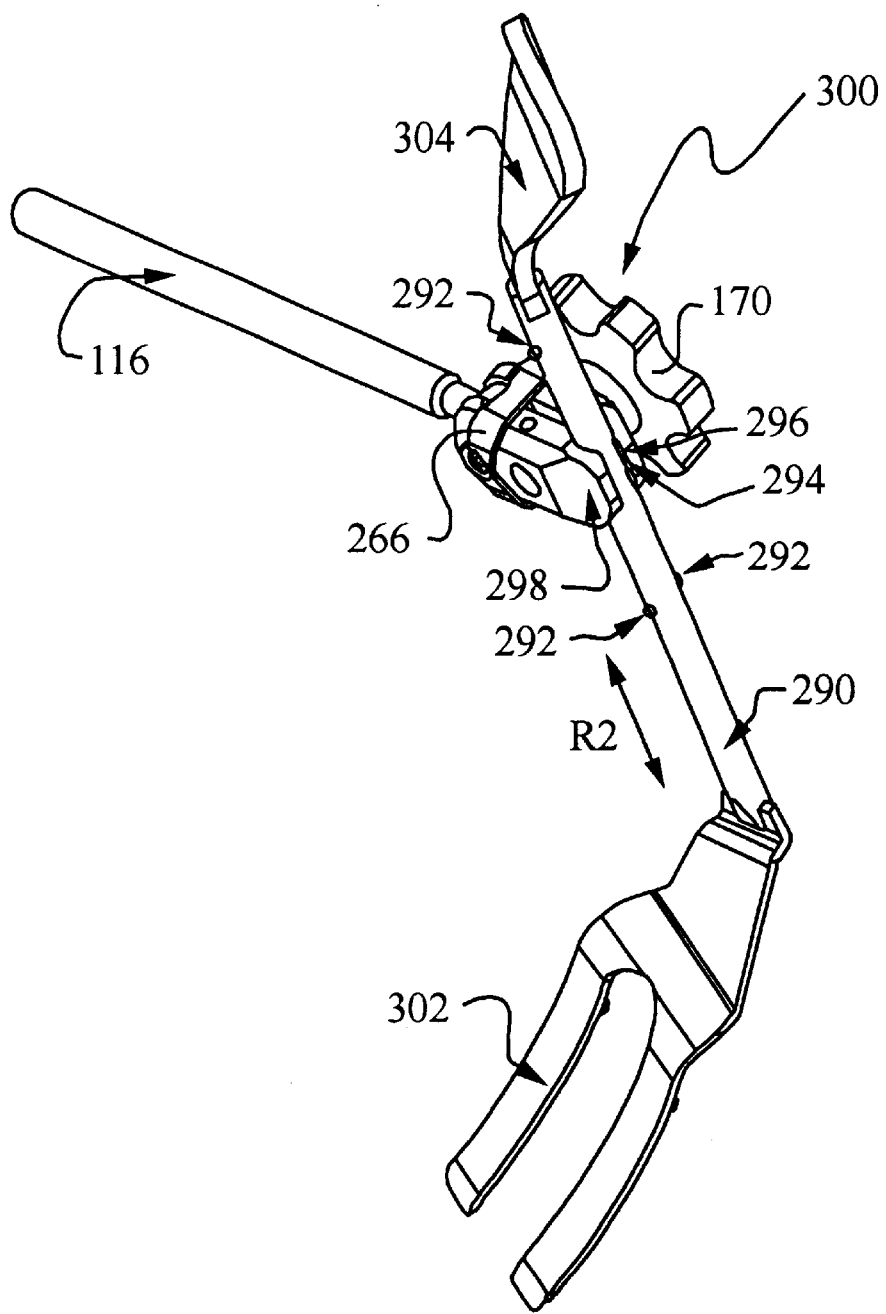
FIG. 10 is a perspective view a further alternative embodiment to that of FIG. 1.
Figure 11:
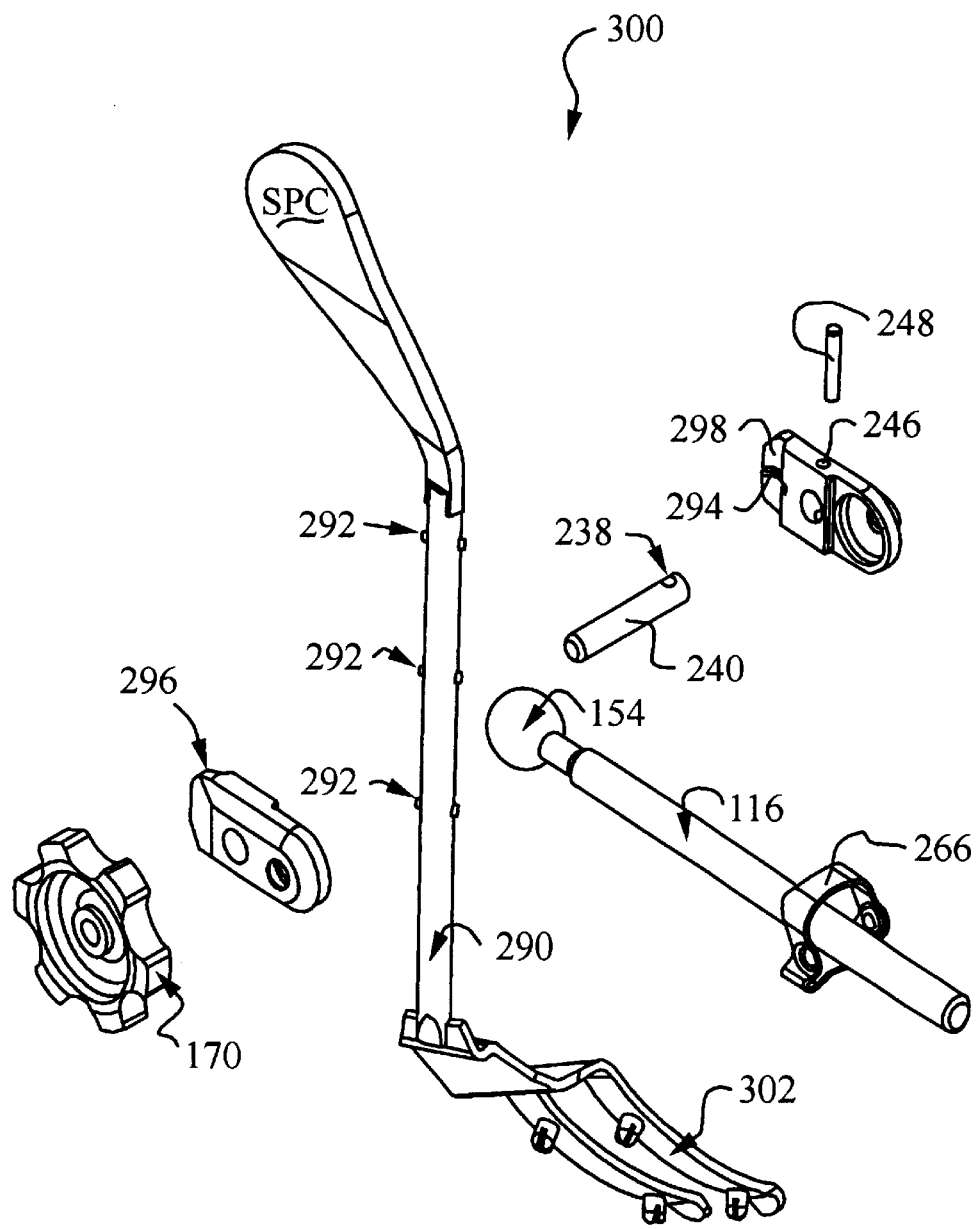
FIG. 11 is an exploded view of the embodiment of FIG. 10.

FIGS. 10 and 11 illustrate a further embodiment of spherical clamp elbow joint 300. In this embodiment shaft 290 has a plurality of spaced pairs of pin-like heads, or stubs, 292 extending therefrom, for engagement with an arcuate circumferential slot or groove 294 formed in one or both of jaws 296 and 298. The adjustment means relationship is obtained from the inter-action of the pin-like features, stubs 292, and the adjustment groove, 294 in the surface of jaws 296 and 298. Bias H2 is achieved when a stub 292 is engaged within a groove 294 of either jaw 296 or 298. Readjustment of bias H2 is achieved without disengaging shaft 290 from the spherical clamp member, elbow joint 300 generally. The contacting means, namely hand 302, is rotated in direction A2 preferably by use of the manipulation means, namely handle 304, such that stub 292 is aligned within the open-ended portion of elbow joint 300. The shaft 290 can then be translated axially in direction R2 until a next series of pin-like stubs 292 are placed in line with groove 294 to engage next biased position H2. The device tends to function much like a key way concept, whereby only at a strategic A2 rotation can the stub 292 on shaft 290 disengage groove 294, preferably by an angular rotation which lies outside the range of angular orientations that may tend to be encountered during heart manipulation within the surgical working volume, "W".

Figure 12:
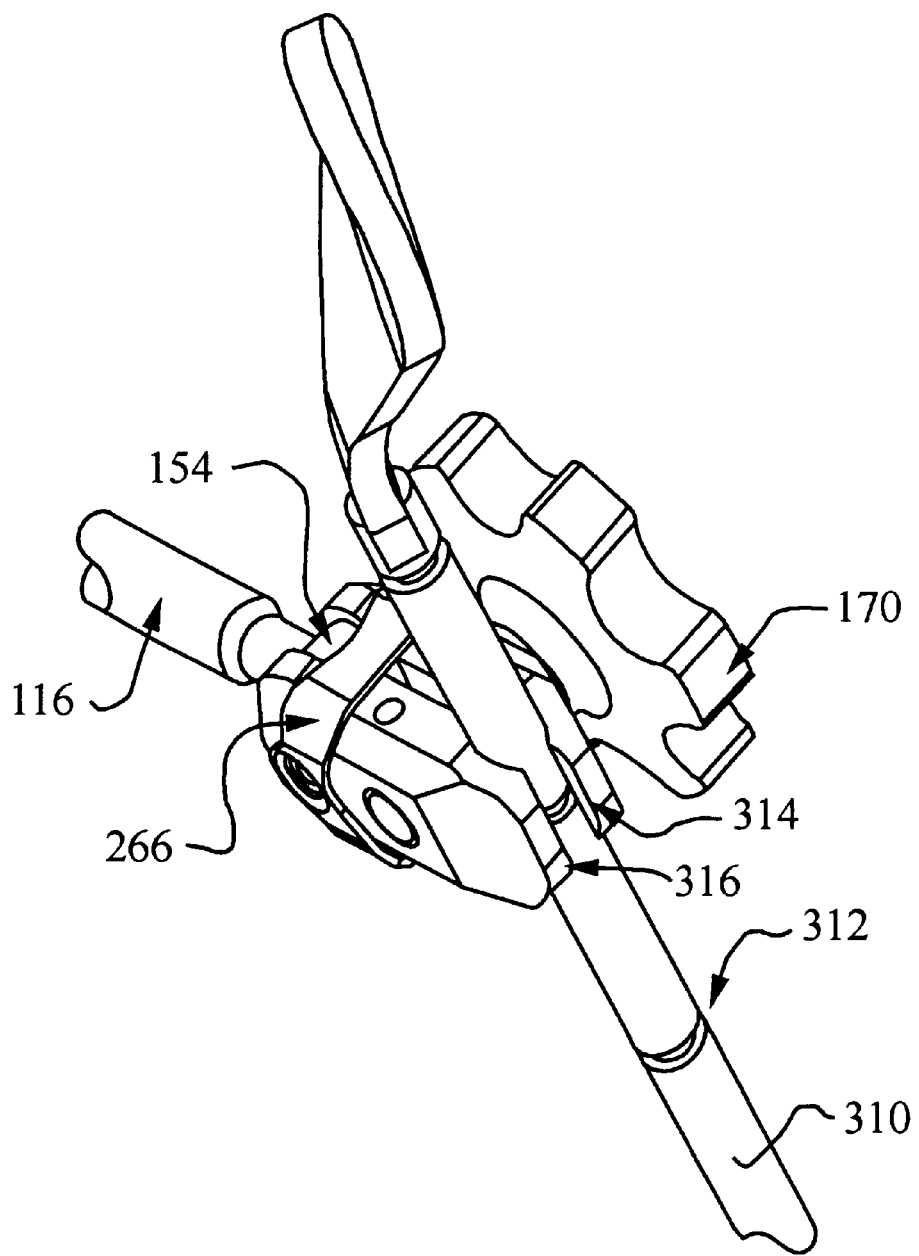
FIG. 12 is a perspective view of a still further alternative embodiment to that of FIG. 1.
Figure 13:
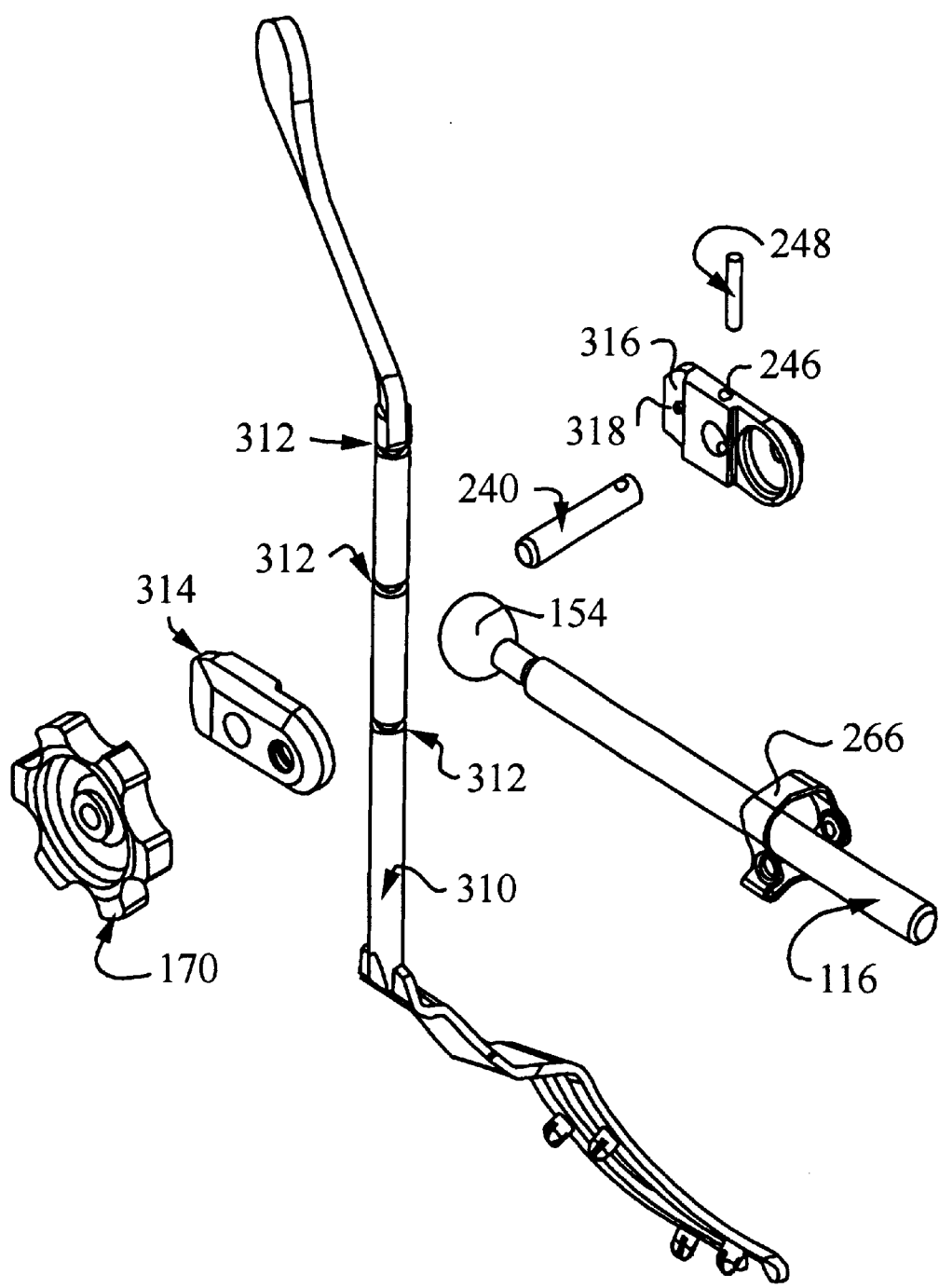
FIG. 13 is an exploded view of the embodiment of FIG. 12.

FIGS. 12 and 13 illustrate still another embodiment of elbow joint suitable for use in an apparatus such as the apparatus of FIG. 1. In this instance, shaft 310 is provided with spaced grooves 312, and jaws 314 and 316 are provided with radially inwardly extending pins 318 for engaging grooves 312.

In each of the embodiments discussed, the multiple degree of freedom nature of articulated arm assembly tends to permit the body tissue contacting means, such as hand 122 to be placed with acceptable accuracy in a wide range of positions and orientations within surgical working volume W. The coarse positioning of the contacting means is preferably obtained through displacements S, R1, A1, and P1. The fine orientation of the contacting means may tend to be achieved mainly through the displacements R2, A2, $\epsilon$, and $\phi$.

The coronary organ contacting means, hand 122 of stabilizer tool 120 is positioned and oriented through the second articulation rod shaft 126 as it interfaces with the spherical clamp of elbow joint 118. The contacting means can exist in a variety of shapes, sizes, and configurations, more specifically "push-type" and "pull-type" configuration. This surgical apparatus, as described in Canadian patent application 2,216,893, is acceptable for the great majority of beating heart CABG surgeries.

In the embodiments of multiple degree of freedom clamps described herein, the side frames are, in the partially tightened, or loose, condition, free to float relative to one another, subject to the constraints of the threaded stud shaft. This floating is limited by the retaining function of the main spring, whether 182, 266 or some other type of spider form, which permits a limited range of motion while maintaining the general configuration of the device. The nature of the attachment interface between the upper arm shaft and its spherical end termination, and the co-operating, floating, split socket halves of the side frames is a capture interface relationship. That is, once the side frames are loosely located in place about the spherical end termination, and the retainer is slid into place (usually under a spring pre-load), the spherical end termination cannot escape from the grasp of the socket halves. Although the male part, the spherical end, is shown on the shaft, and the socket halve co-operate to form a female part, the same kind of capture relationship can be obtained by other arrangements, including a split male part spring loaded to expand within a female socket mounted to the upper arm. The spring loaded ears tend to cause the socket halves to bear against the spherical surface in the partially tightened condition whether the jaws are occupied or not. The float permitted is not sufficient to permit the capture interface with the one structural member, the upper arm, to come apart while the retainer, such as spring 182, is in place. At the same time, the float permitted at the other interface, for engaging the second structure, namely at the jaws, is sufficient to permit the tool shaft to be introduced or removed when sufficient force is applied to overcome the resisting biasing force of the spring. In each case while several degrees of freedom of motion may be permitted in the partially tightened state, tightening of the single tightening member, the knob, fixes the two structural members, that is the upper arm and forearm, in a rigid position with no degrees of freedom at the joint.

Figure 14:
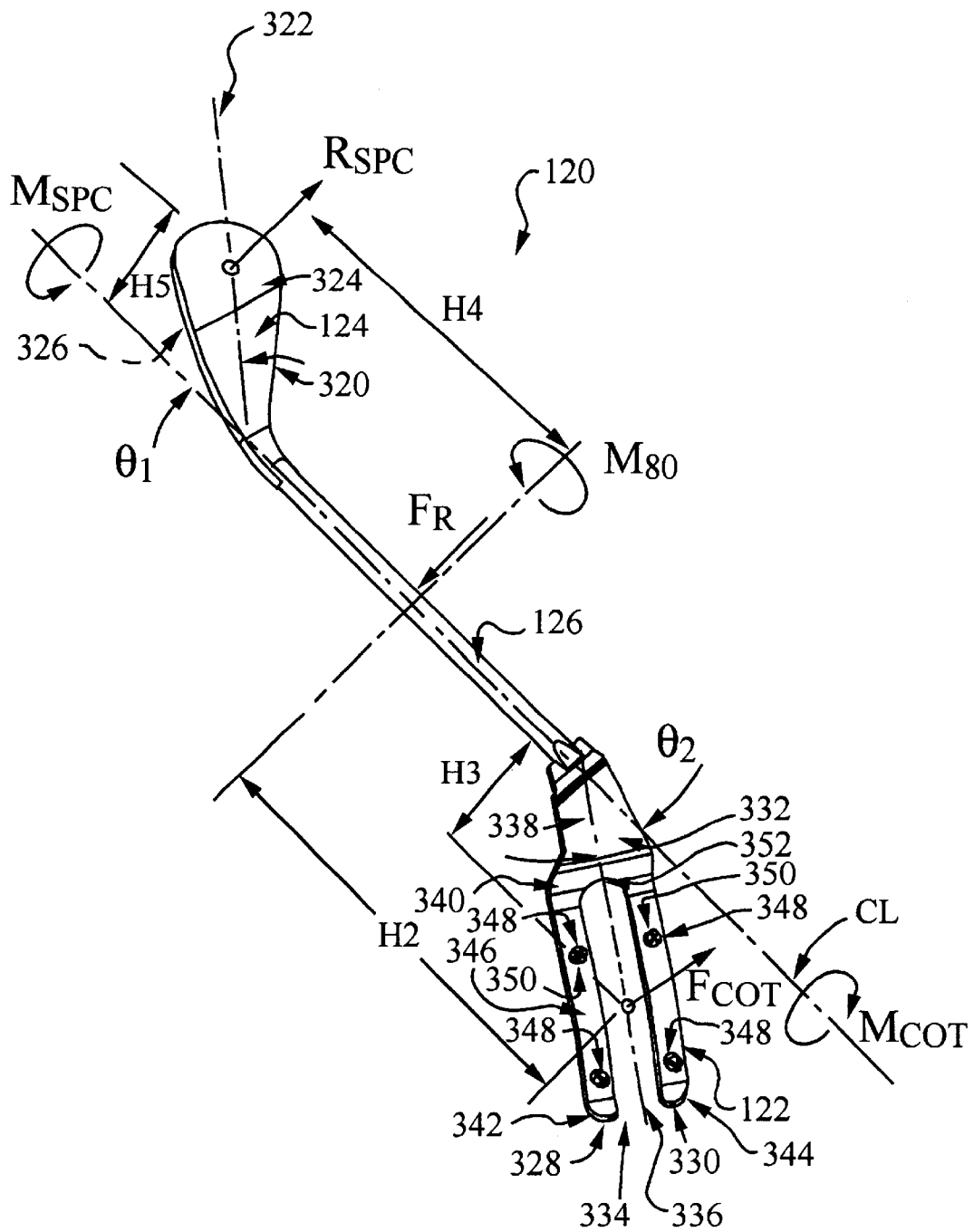
FIG. 14 is a perspective view for defining geometric terminology applicable to the apparatus of FIGS. 1 to 13.

FIG. 14 illustrates geometric terms as defined in relation to a pull-type heart stabilizer, such as heart stabilizer tool 120, which, in general terms has three major components, the body contacting member in the nature of stabilizer hand 122, single point control manipulating handle 124, and shaft 126, also referred to as the second articulation rod. As illustrated, stabilizer hand 122 is a pull type stabilizer, or contacting means, that may tend to be suited for posterior artery revascularization on a beating heart, as described below. A pull-type stabilizer is so named because, in addition to any moment it may transmit, in operation, shaft 126 will tend to be in tension, exerting a force to pull handle 124 against, for example, a portion of the heart. A steep angled pull handle will tend to have a greater proportion of its load in tension than a cantilever-like shallow angled pull-type handle. A handle of this type will tend to extend away from the target artery in a direction that is generally rearwardly of the target artery surface of the heart. This may tend to enhance surgical access to the arterial window, by leaving the working access view of the arterial window unobstructed. It may also tend to permit a surgeon to obtain access to a lower side, or posterior portion of the heart.

With reference to FIG. 14, the force from the beating heart on the contacting member $F_{COT}$, imposes a moment $M_{COT}$ about the centerline CL of, for example, shaft 126. The design of the single point control handle is preferably in a diametrically opposite configuration and complex angle about the centerline of shaft 126, to the contacting member. Through the manipulation handle, the surgeon may tend to be able to sense and react to the forces of the beating heart with $R_{SPC}$ and moment $M_{SPC}$. While the elbow joint is still loose, or not fully tightened past its first tightening level, the force the surgeon feels is also a function of the bias H2 during the specific surgical set-up. When the elbow joint is fully tightened to its second level of tightness, the reaction to $F_{COT}$ imposed at hand 122 will include a moment $M_{SO}$ at the spherical clamp or elbow joint, having one moment component about an axis perpendicular to CL resulting from the product of $F_{COT}$ and a moment arm of length, or bias, H2. The moment at the elbow joint will also include a moment component due to $F_{COT}$ taken at a moment arm corresponding to the eccentricity, H3, of force from centerline CL of shaft 126. Thirdly, when clamped tight, the elbow joint will exert a reaction force of $F_R$ equal in magnitude to of $F_{COT}$, and opposite in direction. The longitudinal moment arm from the fulcrum at the elbow joint to the handle is notionally indicated as H4. The eccentricity of the handle is notionally indicated as H5. For more manipulation control, larger ratios of H4 to H2, and H5 to H3 are preferred. The ratio of H4 to H2 can be adjusted by the surgeon; the ratio of H5 to H3 is fixed by the geometry of the device. The moment arms are notional in the sense that the center of force in each case is taken to be representative of a force distribution either by a body part, such as the heart over the contact surface generally, or by the force of surgeon's hand spread over a significant area of the surface of the handle.

Considering handle 124 as representative, the handle itself is welded to proximal end of shaft 126 and has a flared body 320 whose notional centerline 322 is deflected at a skewed angle $\theta_1$ from centerline CL, such that an eccentric moment can be exerted through handle 124, as discussed above. Body 320 has a first face 324 and a generally oppositely facing second face 326 (shown by a hidden arrow) such that a surgeon's thumb and fingers can engage opposite faces and thus manipulate the tool. Although face 324 is shown to be generally planar, this need not be the case.

At the opposite, distal end of shaft 126, hand 122 is shown as fabricated from stainless steel sheet. It has body-contacting portions in the nature of a pair of fingers 328 and 330 joined by a yoke 332, the fingers defining between them an arterial window, indicated generally as 334. Although fingers 328 and 330 are parallel, this is not a necessary condition for defining an arterial window. An arterial window can have two, three or four sides, or more, or can be defined by an oval, circular, elliptical or other shaped opening, whether having a closed periphery, or a periphery open at one or more sides. Fingers 328 and 330 are for placement to either side of a vein or artery upon which it is desired to perform surgery, with the vein or artery aligned with the notional centerline 336 of arterial window 334.

Centerline 336 is skewed with respect to the centerline CL of shaft 126 at angle $\theta_2$ as indicated. In general, as noted above, it is preferred that the component of the angle of eccentricity of hand 122 that is perpendicular to centerline CL of shaft 126, as defined by centerline 336 of arterial window 334, be generally opposite to the corresponding component of eccentricity of handle 124. They need not be precisely 180 degrees apart, but could be in the range of 135 to 180 degrees apart.

Yoke 332 has a root portion 338 welded to shaft 126, and a bent, stepped portion 340 joining root portion 338 to the proximal ends of fingers 328 and 330. Root portion 338 is substantially offset from fingers 328, 330 in height away from contacted tissue to avoid pressing down on and occluding the target artery which is straddled by the fingers. U shape cut out 352 is deep enough in stepped portion 340 to clear the target artery straddled by fingers 328 and 330. The length of root 338 along axis 336 is sufficiently long to offset shaft 126 away from the heart surface when using pull type stabilizer. Fingers 328 and 330 are sometimes referred to as ski-like, in reference to their rounded distal tips 342 and 344 that are bent to stand away from the body contacted surface, such as the heart, in use. Each of fingers 328 and 330 has a first, or body contacting surface, facing into the page in FIG. 14, and a second, exposed surface 346 for facing away from the body part in use.

As shown, an array of surgical wire attachment fittings, in the nature of upstanding nipples, or posts, 348 are mounted to extend outwardly of surface 346. Each post has a pair of crossed slots 350 for receiving a surgical wire, in the nature of a silastic wire, therein. The slots are angled with respect to centerline 336 of arterial window 334. The slots are wide enough to admit a stretched silastic wire, but when the end of the silastic wire is released, it expands and is captured in the slot. When a silastic wire is located either under a vein or artery, to urge it to stand proudly in the arterial window, or looped about a vein or artery to restrict blood flow, and is anchored in one or more of slots 350, a modest pull on an exposed end can increase the tension in the silastic wire, and adjust its position. Alternatively, a modest pull in the other direction can loosen the wire. As illustrated, stabilizer tool 120 has two pairs of slotted posts 348, such as may permit upstream and downstream silastic wire loops to be placed about a vein or artery and fastened on opposite sides of the arterial window. Alternatively, helical wrapping of silastic wire about the artery can also be achieved.

As described above, the manipulation means, in the nature of a single point control stabilizer, such as stabilizer 120 tends to provide the surgeon with a single control point manipulation handle through which all the degrees of freedom of the surgical apparatus can be set through strategic movement of the single control point handle. This tends to enable positioning and orientation of the contacting means, such as heart stabilizer hand 122, in most, if not all locations within working volume "W". It may also tend to enhance the sensitivity and manual dexterity of the surgeon to the coronary organ tissue load exerted on the contact means during device manipulation. This may tend to reduce the likelihood of inflicting tissue trauma and may tend to improve the chances of hemodynamically stable manipulations of the coronary organ tissue, especially during beating heart surgery. In beating heart CAGB, the pull-type heart stabilizers can be deployed with a complex angle between the heart contacting member and the articulation rod, shaft 126. This may tend to reduce the risk of trauma.

Figure 15A:
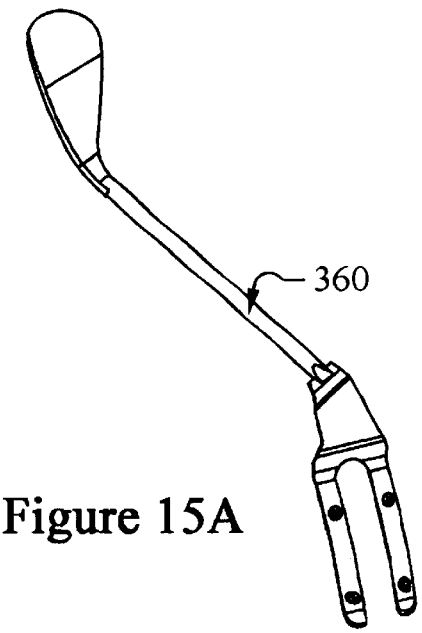
FIG. 15A shows a right hand example of a pull type heart stabilizer of the apparatus of FIG. 1.
Figure 15B:
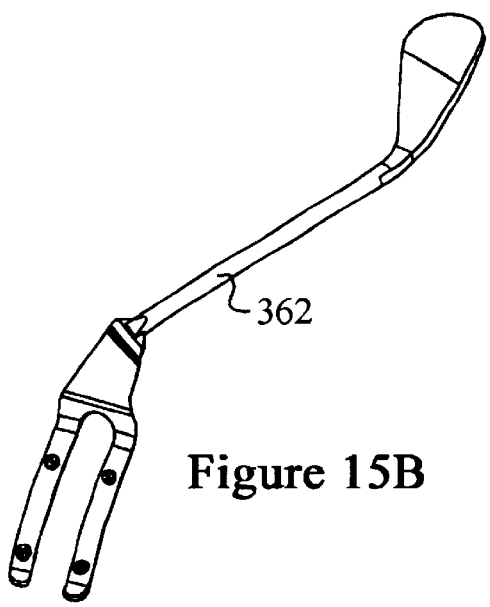
FIG. 15B shows a left hand example of a pull type heart stabilizer of the apparatus of FIG. 1.
Figure 15C:
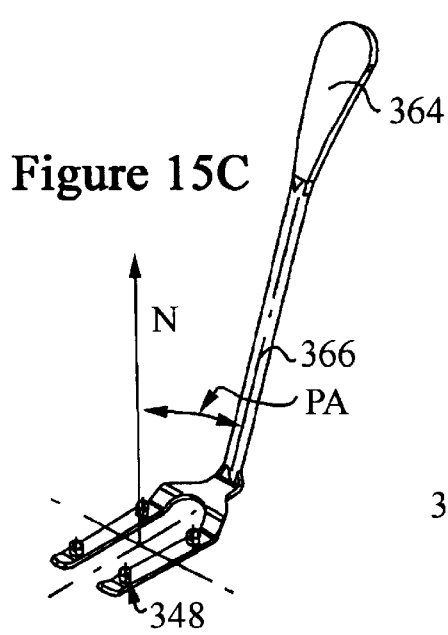
FIG. 15C shows a steeply handled push-type heart stabilizer for use in an apparatus similar to the apparatus of FIG. 1.
Figure 15D:
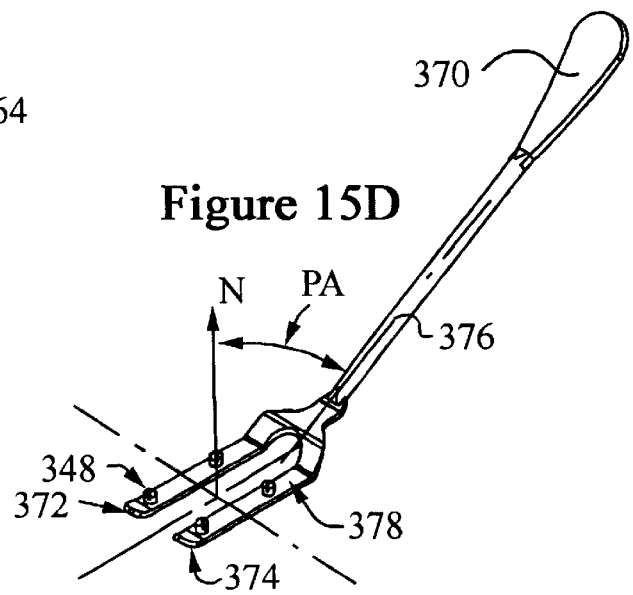
FIG. 15D shows a shallow angled push type stabilizer for use in an apparatus similar to the apparatus of FIG. 1.

The enlarged end of flared body 320 of the single point control (SPC) handle, as shown in FIG. 14, is designed to be engaged by the fingertips of the surgeon while wearing surgical gloves. It can exist in a variety of different sizes, shapes, and angular orientation with respect to centerline of shaft 126, depending on the type of stabilizer or more generally, the type of cardiac device contacting means. FIGS. 15A, 15B, 15C and 15D show alternative examples of SPC handles as a function of different heart stabilizer contacting means. FIG. 15A shows a pull type, right-hand heart stabilizer tool 360, similar to tool 120. FIG. 15B shows a left-hand pull-type stabilizer tool 362. FIG. 15C illustrates a push type, steep angled stabilizer tool 364, in which, typically, shaft 366 will carry a component of force in compression, as well as a moment. A low-angled push type stabilizer 370 is shown in FIG. 15D. A normal vector N is defined as the normal to an ideal body surface, such as heart tissue HT, contacted by fingers 372 and 374. It is desirable for shaft 376 to extend away from hand 378 at a shallow polar angle PA, that is, at a large angle from normal N, to improve visibility and access to the arterial window 379. Although fingers 372 and 374 are shown as being flat, such that the ideal surface defined by them would be a plane, a non-planar ideal surface, and normal thereto, can generally be defined as the normal to the surface curvature, at the center of the arterial window. It is preferred that the angle between normal N and the centerline of the shaft, such as shaft 376, be greater than 45 degrees, and preferably between 60 and 90 degrees or less. A steep push type stabilizer is one having a polar angle, PA less than 45 degrees. A pull-type handle, by this definition, has a polar angle from the normal of greater than 90 degrees, and preferably in the range of 110 to 135 degrees.

Figure 24A:
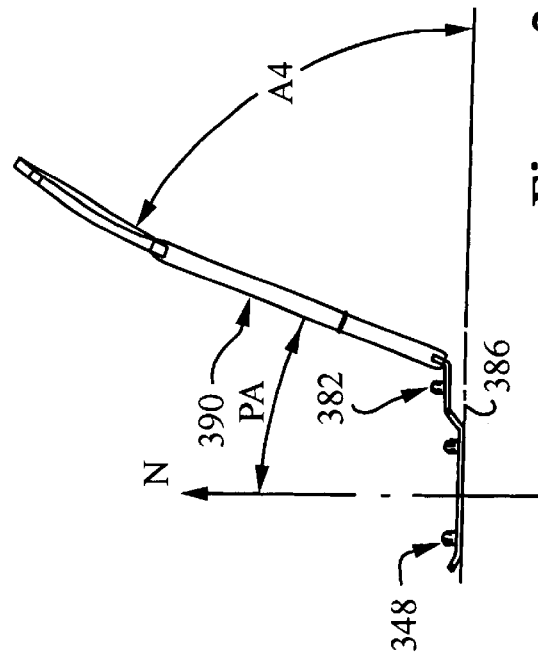
FIG. 24A shows a side view of a steep angle push type coronary stabilizer for use in the apparatus of FIG. 1.
Figure 24B:
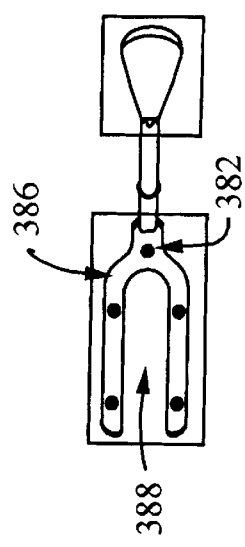
FIG. 24B is a plan view of the stabilizer of FIG. 24A.
Figure 24C:
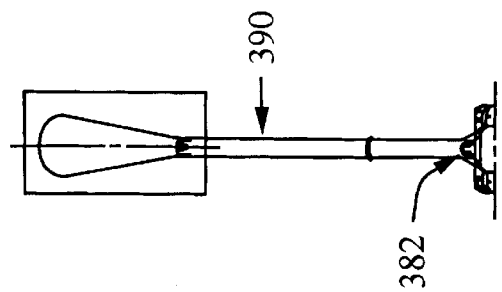
FIG. 24C is a front view of the stabilizer of FIG. 24A.
Figure 25B:
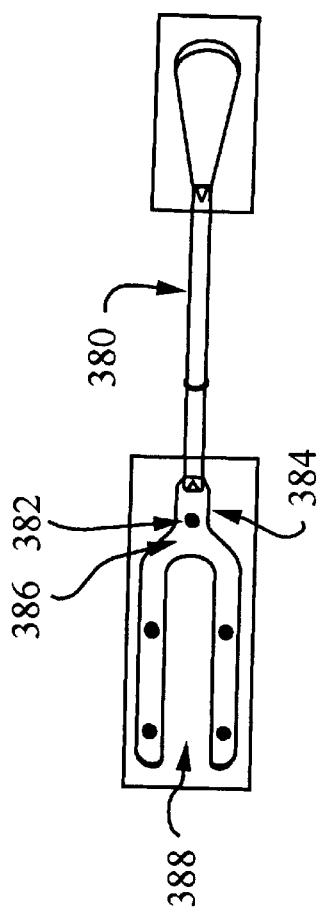
FIG. 25B is a plan view of the stabilizer of FIG. 25A.
Figure 25A:
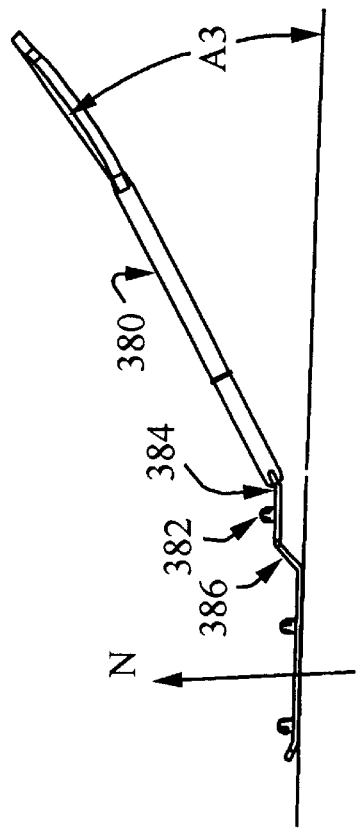
FIG. 25A is a side view of a shallow angle push-type stabilizer for the apparatus of FIG. 1.
Figure 25C:
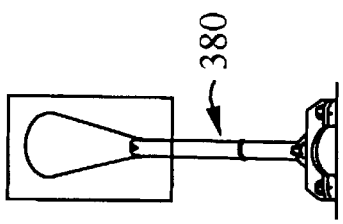
FIG. 25C is a front view of the stabilizer of FIG. 25A.

A push type stabilizer handle 380 similar to push type stabilizer tool 370, is illustrated in side, top and front views in FIGS. 25A, 25B, and 25C respectively. It differs from stabilizer tool 370 in that a fifth surgical wire attachment fitting, in the nature of a slotted post 382, is mounted to extend outwardly from the exposed face, or exposed surface, of the outwardly stepped root portion 384 of yoke 386, adjacent the base of the U of the U-shaped perimeter of arterial window 388. It has a polar angle of 60 degrees. That is, the angle from the horizontal, A3, is 30 degrees. The slot of single post, particularly in the position of crotch post 382, can be used to hold both ends of a loop of silastic wire, thus permitting a loop to be formed about a vein or artery and anchored at a single point. By contrast, a steep angled handle 390 similar to tool 364 is shown in FIGS. 24A, 24B and 24C. It has a polar angle PA of roughly 20 degrees. That is, angle A4 for the horizontal is 70 degrees.

Another pull type stabilizer tool 400 is shown in FIGS. 26A, 26B, 26C, and 26D. It has external circumferential ridges 402, spaced along a shaft 404, as discussed above, for co-operation with an elbow joint. FIG. 26B shows a true view of the angle of eccentricity A5 of the center line 405 of arterial window 406 from the projection of the centerline of shaft 404 in plane 'P1' as indicated in FIG. 26A, and also of the generally corresponding angle of eccentricity A6, as similarly projected, of handle 408. FIG. 26C is a true side view of shaft 404, showing the angle of lie A4 from the horizontal of roughly 32 degrees, implying a polar angle from normal N of 122 degrees. FIG. 26D shows a view perpendicular to plane P2 of FIG. 26A.

Figure 27B:
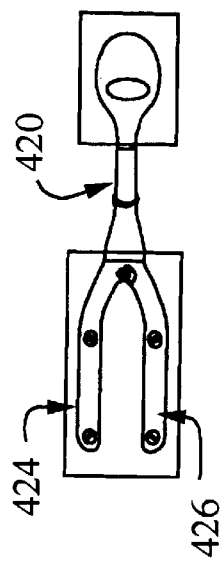
FIG. 27B is a plan view of the stabilizer of FIG. 27A.
Figure 27A:
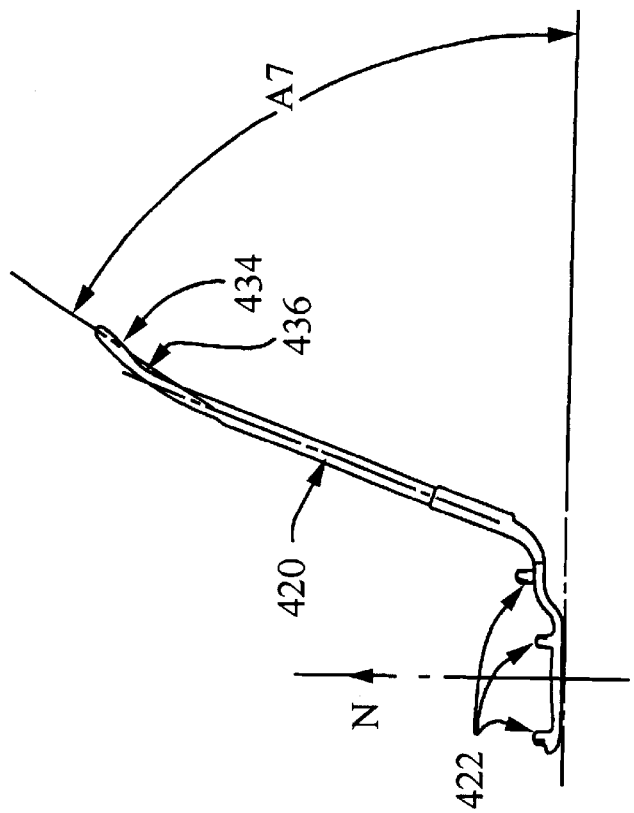
FIG. 27A is a side view of a steep angled push type stabilizer for the apparatus of FIG. 1.
Figure 27C:
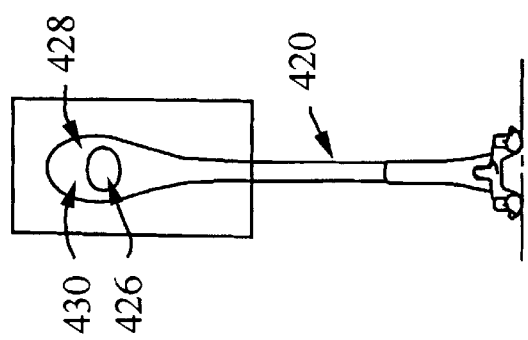
FIG. 27C is a front view of the stabilizer of FIG. 27A.
Figure 28B:
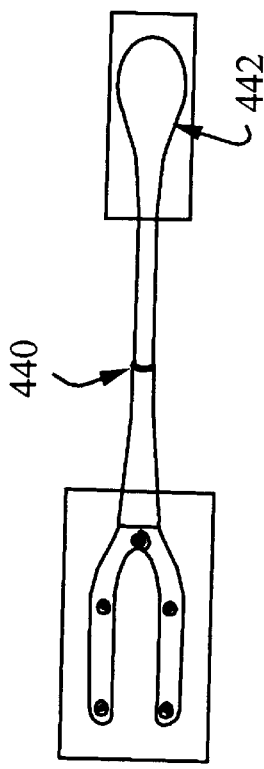
FIG. 28B is a plan view of the stabilizer of FIG. 28A.
Figure 28A:
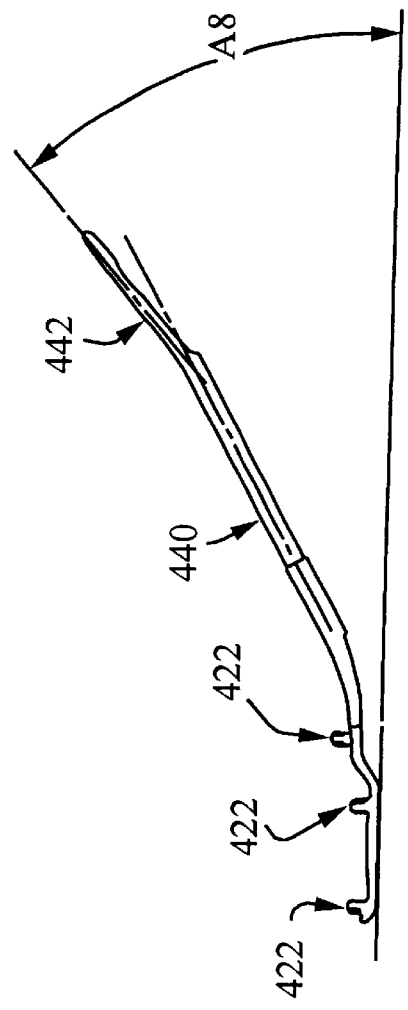
FIG. 28A is a side view of another shallow angled stabilizer for the apparatus of FIG. 1.
Figure 28C:
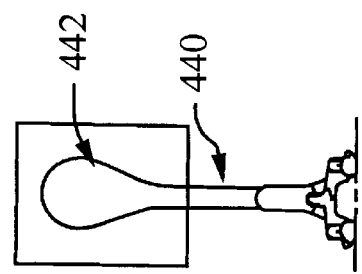
FIG. 28C is a front view of the stabilizer of FIG. 28A.

FIG. 27A shows a steep angled push type stabilizer tool 420 in side view. Tool 420 is a cast stainless steel tool, having attachment fittings, in the nature of posts 422 formed integrally therewith, and having machined slots formed therein. Fingers 424 and 426 have a contoured surface. Handle 428 has one surface 430 having a finger engagement dimple 432, and an opposite surface 434 having an opposed finger engagement dimple 436. The steep lie angle A7, is approximately 70 degrees from the horizontal in this example embodiment. FIGS. 28A, 28B and 28C show side, plan, and front views of a shallow angle, push type cast stabilizer tool 440 having a lie angle A8 from the horizontal of about 30 degrees, and an upwardly kinked handle 442. FIG. 29B shows a side view of a cast stainless steel dog-legged, pull type stabilizer tool 450 taken perpendicular to centerline 452 of arterial window 454, showing the setback D1 of handle 456 from body contact surfaces 458 of fingers 460. FIG. 29A is taken perpendicular to FIG. 29B, and shows the lateral offset D2 of handle 456 from centerline 452. FIG. 29C shows an end view of tool 450 taken perpendicular to both FIGS. 29A and 29B. Shaft 462 has externally protruding circumferential ridges 464 as noted above.

FIGS. 16A to 16E illustrate alternative examples of stabilizer tool proximal end manipulation means in the nature of handles lever arms, or cranks, that are detachable. As shown in FIG. 16A a stabilizer tool is indicated generally as 500. It has a hand 502 and a shaft 504, generally similar to those of stabilizer tool 120. They differ from it inasmuch as handle 506 is detachable from proximal end 508 of shaft 504. As shown in FIG. 16B, proximal end 508 is a male end having a torque transferring feature in the nature of a shank having a generally hexagonal sectional shape, terminating at an inwardly located shoulder 510. A circumferential groove 512 is located intermediate shoulder 510 and the tip of end 508. Handle 506 has a female hexagonal socket 514 for engaging male end 508. As shown in FIG. 16C, handle 506 has a spring-loaded ball detent 516 mounted to engage groove 512, thus encouraging handle 506 to be retained in place relative to shaft 504. This spring loaded detent can be overcome by a modest pulling force when it is desired to detach handle 506. Alternatively, as shown in FIGS. 16D and 16E, other forms of detent can be used. For example, a V-shaped spring clip 518 could be used, or, more securely, a threaded cross-bore 520 and thumbscrew 522 permit a positive tightening force to be applied. Although shaft 504 is indicated as having the male connector portion, and handle 506 the female, a connection interface of this nature can be achieved with the male and female portions reversed, having the female socket on the shaft, for example.

The SPC handle, handle 506, is insertable on the torque transferring feature on the proximal end of shaft 504 in more than one angular position, as may be desired by the surgeon. The torque-transmitting feature can be a hex drive, a spline, a keyway, or other geometry that achieves a mechanical lock between the shaft and the detachable SPC handle. The detachable handle performs and achieves the same function as a fixed, integrally formed handle with shaft, but gives the surgeon the ability to detach it during surgical interventions, once the surgical set-up has been secure, thereby tending to permit a less hindered workspace.

FIGS. 17A to 17D illustrate the concept and design of bias applied to RI; that is, the translation of upper arm 116 with respect to the first articulation member, namely shoulder joint 114, also referred to as the cylindrical post.

FIG. 17A shows an exploded view of shoulder joint 114. A machined puck, or disc 530 has a central bore 532 formed therein to accept shaft 152 of upper arm assembly 116. A slot 534 is formed in one face of disc 530 and extends fully through to intersect bore 532 longitudinally. Disc 530 is sandwiched between a pair of foot and head, hook-like link members 536 and 537, each having a sidearm 538, 539 terminating in a distal overhanging hook 540, 541, each hook having an inner, arcuate surface 542 or 543 for bearing against a portion of the circular cylindrical outer wall 544 of disc 530. Foot member 536 has an attachment fitting 546 with a disc shaped foot mounted on a narrower shaft, foot member 536 being of a size to engage channels 132, 134 or trackway 138. Head member 537 has a threaded stud 548 extending from the end opposite hook 541. A generally circular cylindrical housing 550 is slotted at 552, and has an internal wall defining a longitudinal bore for accommodating link members 536 and 537. When those members are in located in the bore of housing 550, disc 530 can be introduced through slot 552 to seat between hooks 540 and 541. End wall 554 of housing 550 has an opening 555 through which stud 548 extends, through a pre-load spring 556, to engage the internal threads of three cornered tightening knob 558. Pre-load spring 556 will tend to maintain a load on the elements of joint 114 even when knob 558 is loose, tending thereby to keep those elements captured within housing 550.

When fitting 546 is engaged, for example, in channel 132, and knob 558 is tightened, a lower shoulder 560 of housing 550 will bear against the overhanging flanges of channel 132. As knob 558 is tightened it draws link member 536 outward to grasp disc 530 more tightly. Disc 530 in compression in turn pushes against link member 536, which draws the foot of fitting 546 against the underside of the overhanging flanges of channel 132. As these overhanging flanges are squeezed between shoulder 560 and fitting 546, all of the slack in shoulder joint 114 is taken up, slot 534 permitting disc 530 to squeeze shaft 152 tightly, thereby clamping it in place. Thus, a single fastening member can be tightened to seize all of the degrees of freedom of the joint at one time. When loose shoulder joint 114 can move in planar translation along, for example, channel 132, it can permit translation of shaft 152 along its axis relative to bore 532, it permits pivotal motion about the long axis of circular cylindrical housing 550, it permits variation in angular elevation of shaft 152 by pivotal motion about the central axis of disc 530, and it permits rotation of shaft 152 about its own longitudinal axis. Thus five degrees of freedom can be controlled with a single clamp.

FIG. 17B shows an alternate embodiment of an upper arm, indicated as 570, having an array of circumferential, slope sided grooves 571 on spacings or pitches, indicated as L2, measured from the center of spherical end termination 154. A disc 573, otherwise similar to disc 530, has a transverse bore 574 corresponding to bore 532, and, in addition, a cross-bore 575 perpendicular to bore 574 having a spring loaded ball detent 576 mounted therein for engaging such of grooves 571 as it may encounter. As before, the resistance of the spring can be overcome with a modest push or pull on shaft 577 along its longitudinal axis, and, while the corresponding knob is not tightened, shaft 577 can rotate about its longitudinal axis with ball detent 576 is engaged in one of grooves 571. FIG. 17C shows a variation on FIG. 17B in that an upper arm 580 has an array of spring loaded ball detents 581 located in cross-bores 582 long its length, and disc 583 has an internal, slope sided cavity in the nature of a spherically arced depression 584 for receiving the ball detents.

In both FIGS. 17B and 17C the bias is variable by sliding the rod, that is shaft 577 or shaft 585, through the cylindrical post with more force than is normally required or encountered during normal manipulation of the device during positioning or surgical intervention. This compresses the spring loaded detents, whether item 576 or items 581, as they ride up the sloped shoulders of grooves 571 or depression 584 within the housing passage of disc 573 or 583 during readjustment, allowing deployment of the adjustment means, the detent feature, into the next bias position. This may tend generally to allow re-adjustment without disengaging components or unduly disrupting the surgical set-up. The spring loaded feature can be a ball, a cylinder, or other protruding member capable of engaging in a cam- and cam follower relationship. A wave spring or spring loaded lever can also be used.

FIG. 17D illustrates another alternative of an adjustment means. An upper arm 590 is again provided with an array of circumferential grooves 591 set on a spacing or pitch along the length thereof. In additional, a longitudinal channel, or keyway, or spline in the nature of a groove 591 extends along shaft 593 from its proximal end 594 to its most distal groove 592. Disc 595, otherwise similar to disc 532, is shown in section to reveal a protrusion 596 extending inwardly of the wall of bore 597, at a point roughly mid-way along its length. Protrusion 596 is of a size and shape to be accommodated in longitudinal sliding relationship in groove 592 as shaft 593 moves in longitudinal translation between pitches of grooves 591, during which time it impedes rotation of shaft 593 about its longitudinal axis. In addition protrusion 596 is of a size and shape to ride in such of circumferential grooves 591 as it may encounter, permitting rotation of shaft 593 about its longitudinal axis while impeding translation along it except while aligned with groove 592. It follows that the bias, indicated as L2 is variable by rotating shaft 593 in a manner that aligns the dowel-like feature of protrusion 596 with the longitudinal channel of groove 592, sliding shaft 593 through disc 595, and hence through the cylindrical post assembly of which it is part, and then engaging protrusion 596 in another of grooves 591 to achieve the next bias position. As before, this may tend to allow re-adjustment without disengaging components, or unduly disrupting surgical set-up.

In each of FIGS. 17B to 17D, the limited adjustment means restricts the range of motion of the shoulder joint and upper arm with respect to one degree of freedom of motion, while permitting adjustment with respect to one or more other degrees of freedom. Further, the joint can be in any of three conditions. It can be in its pre-loaded, range limited condition, typically held in place by the resistance of a detent. Alternatively it can be in a change of state condition, either in a detent over-ride condition when sufficient force is applied to overcome the resistance of the detent, or by alignment with a transition feature, such as grove 592, permitting movement to another bias state. In the third alternative, the joint can be in its fully tightened state, when all degrees of freedom are inhibited.

In FIGS. 18A to 18D a similar concept is applied to the angular elevational degree of freedom of the upper arm relative to the longitudinal axis of the cylindrical post, or shoulder joint. In FIG. 18A a cylindrical post, or shoulder joint assembly 600 is shown in exploded form. It differs from shoulder joint 114 in that two incremental position adjustment means in the nature of spring loaded ball detents 601 and 602 are indicated. The first is housed in a bore 603 that extends radially relative to the axis of revolution of disc 604 for engaging suitably formed depressions in arcuate surface 605 of foot hook 606. The second is housed in a transverse bore 607 parallel to the axis of revolution of disc 604, as shown insection in FIG. 18C. In this position detent 602 is in a position to engage any one of an array of depressions 608 formed in the inside wall of hook 606 on suitable angular increments along a pitch circle of the same radius relative to the axis of revolutions of disc 604 as shown in FIG. 18D. In this way, FIG. 18B illustrates adjustment means that is spring loaded features in the nature of detents 601 and 602, that are biased to extend radially outward, or transversely outward, to engage one of a plurality of depressions or ridges in the surface of a cylindrical member. It is not necessary to use both detents 601 and 602 as shown in FIG. 18A, but rather one or the other could be employed, as suggest by FIG. 18B on one hand, and FIGS. 18C and 18D on the other. The depressions need not be portions of a hemisphere, but could be conical counter sinks, or lateral grooves, or radial groove, since the detent balls are constraind by their respective bores.

FIGS. 19A to 19C illustrate a similar concept as applied to a channel or trackway in a sternum retractor. FIG. 19A illustrates a cross-sectional view taken through a retractor roll member, or skirt, such as grip 107 engaged to a cylindrical post assembly 610. Assembly 610 has a preload spring 611 between the underside of threaded knob 612 and the top of cylindrical housing 613. The spring pre-load is sufficient to cause a slider, in the nature of fitting 614 and shoulder 615 to bind on inwardly overhanging flanges 616 of the slide, or rail formed by channel 132, thus encouraging assembly 610 to stay where it is, unless an over-ride force is applied to overcome the resistance due to spring 611 and translate assembly 610 along rail 132, 134, or trackway 138 as the case may be. In the fully tightened condition the assembly is fixed in place. Expressed another way, the adjustment means has a spring trapped between the tensioning knob and the outer hollow cylinder of assembly 610. The spring load compresses the articulation cylinder and places the rails of the slide in compression due to the resultant clamping force exerted by the hollow outer cylinder and the fitting engaged in the slide. In this way the first level of tightness, or "light tightness" is achieved, and is sufficient to keep the cylindrical post fixed with respect to the slide, thereby achieving a sliding bias along S.

In the alternative example of FIG. 19B, a spring-loaded detent assembly 621 is housed in a footing 620 for engagement with depressions 622 formed in the back wall of channel 624. That is, an adjustment means is provided by the interaction of a spring loaded feature, detent assembly 621, mounted substantially integrally with the bottom of the cylindrical member, that is, in footing 625, in a position to engage any one of a plurality of depressions in the bottom of the slide formed by channel 132 (or 134, or trackway 138).

FIG. 19C illustrates adjustment means that include a dowel like feature in the nature of a pin 630 extending outwardly from bottom shoulder 631, parallel to the cylindrical axis of hollow cylindrical housing 632. Channel 633 is provided with a series of spaced sockets 634 for receiving pin 630. To retract pin 630 from a current depression, or socket, and move it to another, tensioning knob 636 must be loosened to allow housing 632 to be raised, thereby allowing lifting of pin 630 from one socket 634, permitting sliding of post assembly 637 to another socket 634, where the adjustment means can again come into engagement.

Figures 20A, 20B:
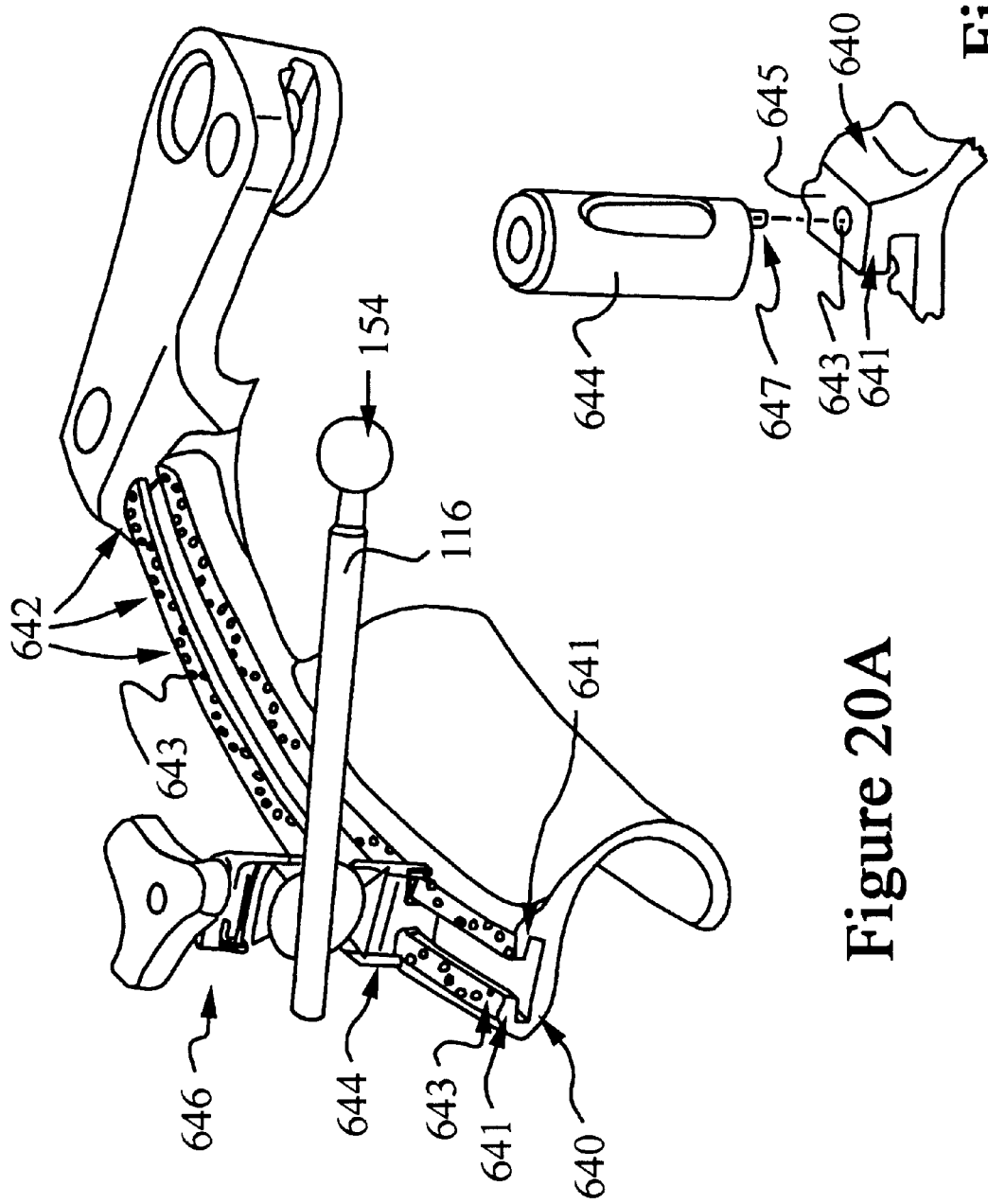
FIG. 20A shows a perspective view of the fitting of FIG. 19C engaged to an adapted sternum retractor.
FIG. 20B shows a detail of the fitting of FIG. 20A.

FIGS. 20A and 20B illustrate a similar concept as applied to limit the range of freedom of motion for a cylindrical post assembly, such as shoulder joint 114, to pivot about the longitudinal axis of its hollow cylindrical member, that is, the axis perpendicular to the trackway, be it channel 132, channel 134 or trackway 138. A slide, rail, or trackway 640 has overhanging flanges 641 having a plurality of arrays 642 of depressions or sockets 643, each array being spaced by a chosen pitch distance along track-way 640, and each array including a plurality of sockets 643 arranged in regular angular increments on a pitch circle whose radius corresponds to the contact radius of the shoulder of a hollow cylindrical housing 644 with the upper surface 645 of trackway 640. A shoulder joint assembly 646 has a pin 647 extending outwardly, not unlike pin 630 noted above, to engage such of sockets 643 as it may be positioned to encounter. This dowel-like pin can be, alternatively, replaced by a spring loaded element, a sheet metal spring or other protruding member capable of engaging a depression such as socket 643, or similar device.

In the embodiments described above, the clamp member, whether it is the shoulder joint or the elbow joint, has one type of indexing feature, and the structural member to which it is to be engaged, whether a trackway of the sternum retractor, the upper arm or the lower arm, has an indexing element, or feature, that co-operates with the indexing feature of the joint. In general, the limitation of motion with respect to one degree of freedom of motion or another to a portion of a larger, full range of motion is indifferent to whether a male indexing feature, such as a protruding bump, pin, stub, or spring loaded ball, is on the joint or on the structural member. Similarly, the corresponding female indexing feature, whether a depression such as a dimple or circumferential groove, a female socket of one type or another, whether biased or not, can in general be applied to either the joint or the associated structural member. In the examples in which one or more of the indexing members is biased to an engaging position, but can be overriden by a sufficient overriding force, in general the biased element can be mounted to either the joint or the connected structural member without departing from the principles of the invention. Similarly, where an element is biased by a resilient member such as a spring, it is possible to employ different types of springs, whether coil springs, leaf springs, belleville springs, torsion springs, or other resilient members.

In each case where indexing features are used to bias one degree of freedom to a particular setting, or a reduced range of settings, the use of such a range, in a partially tightened condition permits a surgeon to hold the position or orientation of the apparatus with respect to one degree of freedom substantially constant, while adjusting orientation or position with respect ot one or more others. Furthermore, the use of a single point control for positioning the body contacting portion of the stabilizing tool, and a single tightening element for fixing all of the degrees of freedom related to a single joint, both at the elbow joint and at the shoulder joint, may tend to facilitate placement of the apparatus by reducing the number of tightening and positioning actions required.

Figure 21:
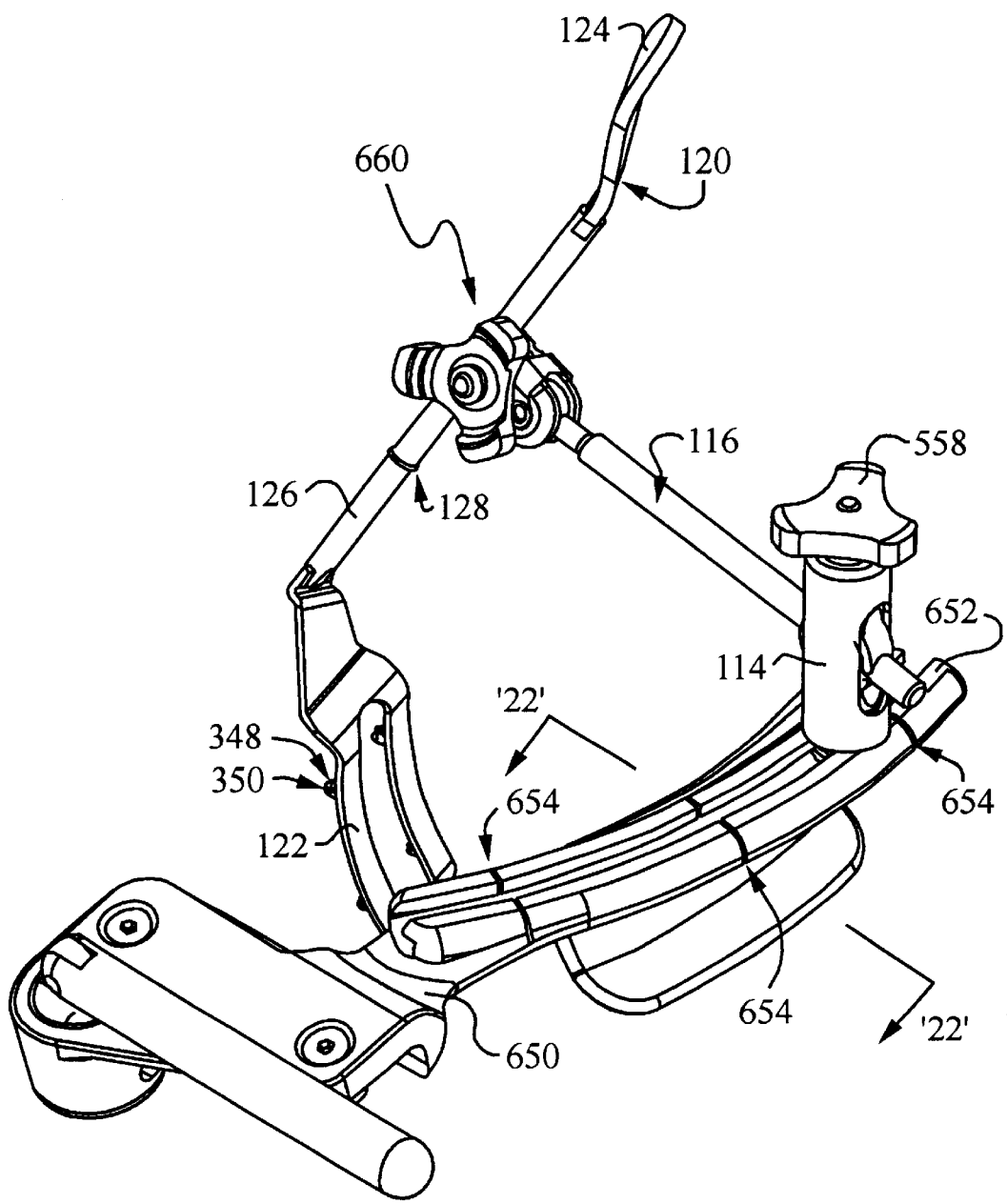
FIG. 21 is a perspective view of surgical apparatus illustrating a slit-like feature in an alternative sternum retractor to that shown with the apparatus of FIG. 1.
Figure 22:
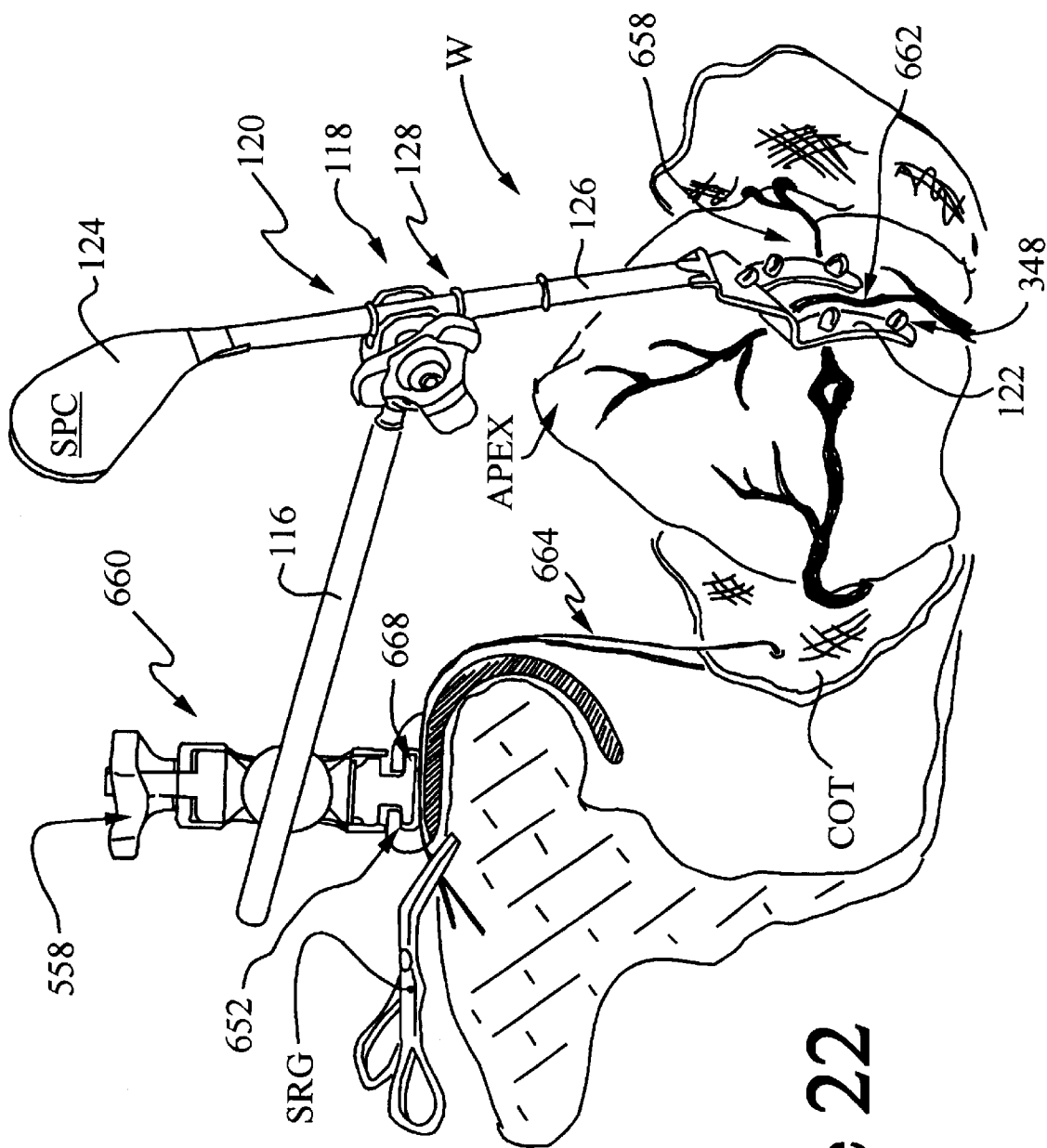
FIG. 22 is a cross-sectional view of surgical apparatus illustrated in FIG. 21 in use.

FIGS. 21 and 22 illustrate an additional alternative embodiment of surgical apparatus. In FIG. 21 shows a right-hand main structural member 650 with an articulated arm assembly 660 mounted thereon. Right hand main structural member 650 differs from right hand main structural member 102 of assembly 100 in that its slide, or trackway, namely arcuate channel 652, while retaining the same cross-section and plan form as channel 134, has in addition an array of surgical wire anchoring features in the nature of transverse slits 654 spaced periodically along its length. Slits 654 each provide a substantially channel-like passage across the rail, that is channel 134, of a base retractor structural member, that is, member 650, that is of a size for accepting one or more surgical wires. That is, slits 654 are formed not merely in the side walls of channel 652, but also in the back, or base wall, so that surgical wire engaged therein can lie shy of the bottom, or floor surface within the slide of channel 652. FIG. 22 is a cross-sectional view taken on section '22—22' of FIG. 21, with the apparatus employed in surgical interaction with a body part, specifically, the heart. The surgical set-up shows the positioning means, namely articulated arm assembly 660, including an upper arm such as upper arm 116, a spherical clamp elbow joint such as elbow joint 118, and a pull-type stabilizer tool such as tool 120 for immobilizing and positioning the posterior portion of the beating heart indicated generally as 658 about a target artery 662 requiring bypass grafting. The set-up also shows a surgical suture 664 used to retract the coronary organ tissue COT, in this case the pericardium, thereby helping to verticalize the beating heart, that is to raise the forward portion of the heart, the apex, the better to expose veins and arteries that would not otherwise normally be visible and accessible for revascularization. The surgical suture 664 can be inserted in slit 654 and anchored behind, that is, in the context of working volume 'W', on the outside of the retractor arm, namely structural member 650 with the help of either a surgical clamp SRG, or other surgical instrument capable of retaining at least one end of the surgical suture and of applying a load to the COT to maintain it in the position shown. The design of the slit-like feature, slit 654 is such that when the surgical suture is inserted therein and lies shy of the floor channel 652, it does not impede the functioning of articulated arm assembly 660, and more specifically the functioning of the cylindrical post, namely shoulder joint 114. Alternatively, the channel may be of sufficient overall depth that the lowest portion of the fitment 668 of shoulder joint 114 passes overhead with a clearance above suture 664. This permits variation of the position of joint 114 along channel 652 as the surgeon or other operator may choose, including directly above surgical suture 664. Although FIG. 22 shows a surgical suture utilized during beating heart CABG, the design and concept applies equally to other types of peripheral surgical equipment (like silicon loops, diagnostic equipment leads, suction cannula) used in CABG or other cardiac surgeries requiring a base retractor. As described at least a portion of the apparatus of FIGS. 21 and 22, and in particular articulated arm assembly 660, can be repositioned and adjusted without disrupting surgical stay sutures or other peripheral surgical equipment within, or extending through, working volume W. As illustrated in FIG. 22, assembly 660 can be seen both to provide access to an underside portion of the heart, but also employs a pull type handle, in a position in which assembly 660 overspans the heart either laterally or rearwardly. In such an orientation assembly 660 may tend not to impede access to the arterial window.

Figure 23:
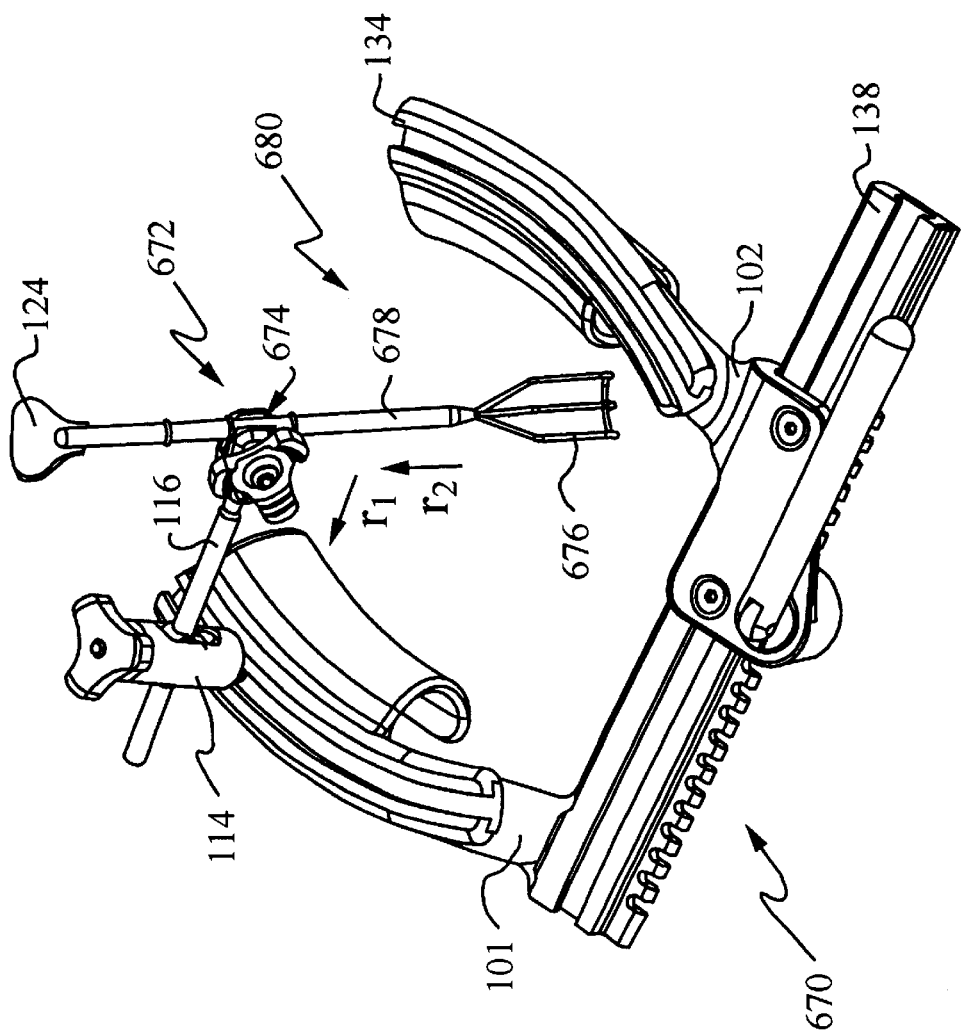
FIG. 23 is a perspective view of an alternative embodiment of apparatus to that of FIG. 1.

FIG. 23 illustrates an additional embodiment of this invention. The design and concepts relating to adjustment means as discussed above, may tend also to be applicable to the surgical apparatus 670 of FIG. 23. FIG. 23 illustrates an adjustment means, in the nature of articulated arm assembly 672, employing a spherical clamp elbow joint 674 and body tissue contacting stabilizer 676, the ridged shaft 678 of stabilizer 676 co-operating with joint 674 in a selected bias position H2 as described in FIG. 9, above. The concepts and designs of the manipulation means as described in FIGS. 14 to 16 also apply to surgical apparatus for, and steps of, cardiac surgery. This includes surgical apparatus used for cardiac surgery, specifically valve surgery. Unlike other valve surgery apparatus, the multiple degrees of freedom permitted by apparatus 670, like apparatus 120, provide a means to allow the contacting means, tissue retractor 680, to apply mechanical loads to the coronary organ tissue. Tissue retractor 680 is used to contact the aorta, if used in aortic valve surgery, or to contact the right atrium if used in mitral valve surgery, along the $r_2$ and $r_1$ direction simultaneously. This allows the COT not only to be retracted towards the perimeter of surgical working volume W, but also to be lifted upward within working volume W thereby improving surgeon access and visibility.

The method of operation of the surgical set-up during cardiac surgery, more specifically beating heart CABG, related to this invention can include the steps of:

1) Setting the positioning means of a cylindrical post, such as the cantilever footing of shoulder joint 114, and setting the position of a spherical clamp, on a base retractor slider or trackway, at an approximate location for providing surgical access, and approach, to a target artery to be revascularized, and which suits the surgeon's preference for the surgical set-up;

2) Selecting a coronary organ contacting means, in this case, a heart stabilizer tool such as tool 120 having a hand for contacting the heart such as hand 122, based on the artery type requiring grafting (whether anterior, inferior, or posterior artery bed), and specific patient anatomy. For example, for a bypass graft on the posterior obtuse marginal artery, the pull-type stabilizer, with left hand bend between the hand and the shaft, is preferred.

3) Selecting a desired bias H2 distance between the contacting member, such as hand 122 and a spherical clamp, such as may, for example, be chosen from the examples of elbow joints illustrated herein and described above. For example, in grafting the posterior obtuse marginal artery, the surgeon will have to "verticalize" heart, and therefore a longer H2 bias is desirable.

4) With tension in the elbow joint knob loosened, inserting the shaft, such as shaft 126 or one of the other embodiments of shaft illustrated herein and described above, within the open-ended spherical clamp.

5) If adjustment lever dog 180 is not engaged in adjustment groove 128, and bias H2 is desired, translating the shaft along R2 until the adjustment features become engaged. Throughout, the shaft remains in contact with interface defined by the jaws of the clamping members.

6) Tightening, slightly, the tightening knob of the elbow joint to restrict the amount clamping members can spread apart while being resisted by their retainer spring. This tends to reduce or eliminate sloppiness in the interface between the forearm shaft and the clamping members, but does not impose any friction or clamping load on the clamping members. The shaft can still rotate freely (A2), and spherical clamp can pivot freely about the spherical end ($\epsilon$, $\phi$).

7) Through manipulation of a single point control (SPC) handle, locating the contacting means, that is, for example, a body contacting member in the nature of hand 122 or other hand illustrated and described herein, in a position or orientation within working volume "W" on a body contact surface, such as a portion of coronary organ tissue. In the case of grafting the posterior obtuse marginal artery, the method includes using the apparatus through the manipulation of the SPC to "verticalize" the beating heart to position and orient the coronary organ tissue within working volume "W".

8) Throughout the surgeon manipulations, all the motion degrees of freedom of the apparatus can be utilized and varied by movement of the single control point handle SPC, some within a limited range if biases are imposed, in order to achieve optimum setting of contacting means and optimum setting of coronary organ tissue within working volume "W".

9) If the bias H2 is not ideal for the surgical intervention, translating the forearm shaft through the spherical clamp. The adjustment means will readjust bias without having to disengage the forearm shaft from the spherical clamp.

10) Completing the location of the contacting means and the coronary organ tissue, by the steps of tightening the elbow and shoulder joints to secure the entire set-up, after which the surgical intervention can proceed. Either knob can be loosened to effectuate in-process readjustments of set-up without having to disengage components or having to undo a large portion of the surgical set-up.

The preceding FIGS. 3, 5, 7, 9, 10, and 12 describe the concept of motion bias within the surgical apparatus, as applied, for example to the forearm shaft and spherical elbow joint clamp to achieve translational bias H2 along R2. These concepts and designs can also be applied to other motion degrees of freedom of the surgical apparatus, by introducing an adjustment means at the interfaces between components which provide motion degrees of freedom desired to be biased.

The surgical apparatus broadly described herein, as it is used in beating heart CABG, may tend to provide the flexibility to the surgeon to achieve efficient access to various target artery types, allows adaptability of device and set-up to different patient anatomies, and permits customization of surgical set-up to suit surgeon preference.

The system is designed for re-usable components, whose assembly can be dismantled for ease of sterilization. The various component items are manufactured in surgical grade stainless steel, titanium, or other re-usable sterilizable material. However, any number of components can also be made in disposable surgical grade plastics, as may be suitable under some circumstances.

A preferred embodiment has been described in detail and a number of alternatives have also been described. As changes in, or additions to, the above described embodiments may be made without departing from the nature, spirit or scope of the invention, the invention is not to be limited by or to those details, but only by the appended claims.

We claim:

1. A surgical articulation assembly comprising:

a first arm, a second arm, and an articulation joint connecting said arms;

said joint being engaged to said first arm;

said joint having a clamp for mating engagement with said second arm;

said joint and said second arm having mutually engageable indexing elements;

said clamp being operable to engage said second arm in a partially tightened condition;

in said partially tightened condition said indexing elements being mutually engaged to encourage said second arm to be restrained to a limited range of motion with respect to one degree of freedom of motion;

in said partially tightened condition said second arm being free to move in a full range of motion with respect to at least one other degree of freedom of motion relative to said first arm; and said clamp being operable to engage said second arm in a fully tightened condition to fix said second arm relative to said first arm.

2. The articulation assembly of claim 1 wherein said second arm is a tissue stabilizing tool having a body contacting portion and a shaft portion rigidly mounted thereto;

said shaft being engageable in said clamp;

said indexing element of said second arm includes at least one depression extending inwardly of the surface thereof; and said indexing element of said clamp includes at least one protrusion for engaging said at least one depression.

3. The articulation assembly of claim 2 wherein in said partially tightened condition said indexing element of said second arm extends circumferentially about said shaft to restrain longitudinal translation thereof relative to said clamp while permitting rotation about a longitudinal axis thereof relative to said clamp.

4. The articulation assembly of claim 2 wherein said indexing element of said clamp is biased to an engagement position and can deflect under an override force to permit motion outside said limited range of motion.

5. The articulation assembly of claim 4 wherein said indexing element is a spring loaded detent.

6. The articulation assembly of claim 2 wherein said indexing element of said second arm is biased to an engagement position and can deflect under an override force to permit motion outside said limited range of motion.

7. The articulation assembly of claim 6 wherein said indexing element of said second arm is a spring loaded detent.

8. The articulation assembly of claim 1 wherein said second arm is a tissue stabilizing tool having a body contacting portion and a shaft portion rigidly mounted thereto; said shaft is engageable in said clamp; and said indexing element of said second arm includes at least one protrusion extending outwardly of the surface thereof; and said indexing element of said clamp includes at least one depression for engagement by said at least one protrusion.

9. The articulation assembly of claim 8 wherein in said partially tightened condition said indexing element of said second arm extends circumferentially about said shaft to restrain longitudinal translation thereof relative to said clamp while permitting rotation about a longitudinal axis thereof relative to said clamp.

10. The articulation assembly of claim 8 wherein said indexing element of said clamp is biased to an engagement position and can deflect under an override force to permit motion outside said limited range of motion.

11. The articulation assembly of claim 10 wherein said indexing element of said clamp is a spring loaded detent.

12. The articulation assembly of claim 8 wherein said indexing element of said second arm is biased to an engagement position and can deflect under an override force to permit motion outside said limited range of motion.

13. The articulation assembly of claim 12 wherein said indexing element of said second arm is a spring loaded detent.

14. A floating clamp assembly for governing the relationship of a first structural member to a second structural member said clamp assembly comprising:

first and second frame members, one of said frame members being mounted in a floating relationship relative to the other;

said frame members having first co-operating portions of a capture fitting for engaging a mating portion of the first structural member;

said frame members having co-operating opposed jaw portions for engaging said second structural member;

a retainer mounted to limit the floating relationship between said frames and to maintain said first co-operating portions in a capture relationship with the mating portion of the first structural member;

in a loosened condition of said clamp assembly, said jaw portions being biased to an engaged position relative to said second structural member by said retainer; and said floating relationship permitting said jaws to deflect to admit a portion of the second structural member;

and, in a tightened condition of said clamp assembly said frame members co-operating to fix the position of the structural members relative to each other.

* * * * *